US009629705B2

(12) United States Patent
Douthitt et al.

(10) Patent No.: US 9,629,705 B2
(45) Date of Patent: *Apr. 25, 2017

(54) DEVICES AND METHODS FOR ANATOMIC MAPPING FOR PROSTHETIC IMPLANTS

(71) Applicant: Aortica Corporation, Bellevue, WA (US)

(72) Inventors: Thomas C. Douthitt, Kirkland, WA (US); Richard Van Bibber, Redmond, WA (US); Arun Palligaranai Tirumalai, Sammamish, WA (US); Prashanth Dumpuri, Kirkland, WA (US)

(73) Assignee: Aortica Corporation, Bellevue, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/291,602

(22) Filed: Oct. 12, 2016

(65) Prior Publication Data

US 2017/0027683 A1   Feb. 2, 2017

Related U.S. Application Data

(63) Continuation of application No. PCT/US2016/041355, filed on Jul. 7, 2016.
(Continued)

(51) Int. Cl.
*G06K 9/00* (2006.01)
*A61F 2/07* (2013.01)
(Continued)

(52) U.S. Cl.
CPC .............. *A61F 2/07* (2013.01); *A61B 34/10* (2016.02); *G06F 19/321* (2013.01);
(Continued)

(58) Field of Classification Search
CPC ...... A61F 2/07; A61F 2240/002; A61B 34/10; A61B 2034/108; G06F 19/3437; G06F 19/321

See application file for complete search history.

(56) References Cited

U.S. PATENT DOCUMENTS 5,370,692 A   12/1994   Fink et al.
7,197,170 B2   3/2007   Dwyer
(Continued)

FOREIGN PATENT DOCUMENTS

WO   WO 02/29758 A2   4/2002
WO   WO 2007/045000 A2   4/2007
(Continued)

OTHER PUBLICATIONS

Chuter, Timothy A.M., "Fenestrated and Branched Stent-Grafts for Thoracoabdominal, Pararenal and Juxtarenal Aortic Aneurysm Repair," Seminars in Vascular Surgery, 2007; 7 pages.
(Continued)

*Primary Examiner* — John Strege
(74) *Attorney, Agent, or Firm* — Cooley LLP

(57) ABSTRACT

A method of generating a patient-specific prosthesis includes receiving anatomic imaging data representative of a portion of a patient's anatomy. A first digital representation of the anatomic imaging data is defined. The first digital representation of the anatomic imaging data is modified. A second digital representation of the portion of the patient's anatomy is defined based on the modifying of the first digital representation of the anatomic imaging data. A patient-specific prosthesis is generated based at least in part on the second digital representation of the anatomic imaging data.

29 Claims, 6 Drawing Sheets

Related U.S. Application Data

(60) Provisional application No. 62/189,918, filed on Jul. 8, 2015.

(51) Int. Cl.
    *A61B 34/10*     (2016.01)
    *G06F 19/00*     (2011.01)

(52) U.S. Cl.
    CPC .... *G06F 19/3437* (2013.01); *A61B 2034/108* (2016.02); *A61F 2240/002* (2013.01)

(56) References Cited

U.S. PATENT DOCUMENTS

| | | | |
|---|---|---|---|
| 7,937,660 | B2 | 5/2011 | Binkert |
| 8,682,626 | B2 | 3/2014 | Ionasec et al. |
| 8,831,302 | B2 | 9/2014 | Mahfouz |
| 8,897,513 | B2 | 11/2014 | Balasubramanian |
| 8,989,460 | B2 | 3/2015 | Mahfouz |
| 9,305,123 | B2 | 4/2016 | Leotta et al. |
| 2004/0102866 | A1* | 5/2004 | Harris ............... G06T 17/00 700/117 |
| 2005/0131518 | A1 | 6/2005 | Hartley |
| 2006/0058638 | A1 | 3/2006 | Boese |
| 2007/0293936 | A1 | 12/2007 | Dobak |
| 2008/0201007 | A1 | 8/2008 | Boyden et al. |
| 2008/0255582 | A1 | 10/2008 | Harris |
| 2009/0204228 | A1 | 8/2009 | Hiles |
| 2009/0304245 | A1 | 12/2009 | Egger et al. |
| 2013/0289690 | A1 | 10/2013 | Thapliyal |
| 2013/0296998 | A1 | 11/2013 | Leotta et al. |
| 2015/0234957 | A1 | 8/2015 | Leotta et al. |

FOREIGN PATENT DOCUMENTS

| | | |
|---|---|---|
| WO | WO 2008/124222 A1 | 10/2008 |
| WO | WO 2013/066880 | 5/2013 |

OTHER PUBLICATIONS

Chuter, Tim, et al., "Standardized off-the-shelf components for multibranched endovascular repair of thoracoabdominal aortic aneurysms," Perspectives in Vascular Surgery and Endovascular Therapy, Sep. 23, 2011, 8 pages.

Elkouri, Stephane, et al., "Most patients with abdominal aortic aneurysm are not suitable for endovascular repair using currently approved bifurcated stent-grafts," Vascular and Endovascular Surgery, 2004, 13 pages.

Hazer, D., et al., "A workflow for computational fluid dynamics simulations using patient-specific aortic models," 24th CADFEM Users Meeting 2006, International Congress on FEM Technology with 2006 German ANSYS Conference, Oct. 25, 2006, 9 pages.

Higashiura, Wataru, et al., "Initial experience of branched endovascular graft for abdominal aortic aneurysm with complex anatomy of proximal neck: planning and technical considerations," Jpn J Radiol, Jan. 28, 2010, 9 pages.

Legget, Malcolm, E., et al., "System for quantitative three-dimensional echocardiography of the left ventricle based on a magnetic-field position and orientation sensing system," IEEE Transactions on Biomedical Engineering, Apr. 1998; 11 pages.

Leotta, Daniel F., et al., "Measurement of abdominal aortic aneurysms with three-dimensional ultrasound imaging: preliminary report," Journal of Vascular Surgery, Apr. 2001 8 pages.

Malina, M., et al., "EVAR and complex anatomy: an update on fenestrated and branched stent grafts," Scandinavian Journal of Surgery, Mar. 9, 2008, 10 pages.

Nordon, Ian M., et al., "Toward an 'off-the-shelf' fenestrated endograft for management of short-necked abdominal aortic aneurysms: an analysis of current graft morphological diversity," J Endovasc Ther., Feb. 17, 2010, 8 pages.

Oderich, Gustavo S., et al., "Modified fenestrated stent grafts: device design, modifications, implantation, and current applications," Perspectives in Vascular Surgery and Endovascular Therapy, Sep. 21, 2009, 12 pages.

Resch, T., et al., "Incidence and management of complications after branched and fenestrated endografting," Journal of Cardiovascular Surgery, Feb. 2010, 8 pages.

Ricotta, Joseph J., et al., "Fenestrated and branched stent grafts," Perspective Vascular Surgery and Endovascular Therapy, Jun. 2008, 15 pages.

Stratasys, Dimension 1200es 3D modeling printer, Durability Meets Affordability, www.stratasys.com/3d-printers/design-series/performance/dimension-1200es, 2014, 4 pages.

UK EVAR Trial Investigators, Endovascular versus open repair of abdominal aortic aneurysm, New England Journal of Medicine, May 20, 2010, 9 pages.

International Search Report and Written Opinion for International Application No. PCT/US2016/041355, mailed Sep. 20, 2016, 12 pages.

International Search Report and Written Opinion for International Application No. PCT/US2016/029185, mailed Jul. 20, 2016, 12 pages.

Official Action for U.S. Appl. No. 13/875,209, mailed Mar. 9, 2016, 16 pages.

Official Action for U.S. Appl. No. 13/875,209, mailed Sep. 8, 2016, 2016, 23 pages.

Official Action for U.S. Appl. No. 14/701,382, mailed Jul. 30, 2015, 7 pages.

Official Action for U.S. Appl. No. 15/163,255, mailed Sep. 20, 2016, 10 pages.

\* cited by examiner

DEVICES AND METHODS FOR ANATOMIC MAPPING FOR PROSTHETIC IMPLANTS

CROSS-REFERENCE TO RELATED APPLICATIONS

This application is a continuation of International Application No. PCT/US2016/041355, filed Jul. 7, 2016, which claims priority to and the benefit of U.S. Provisional Patent Application Ser. No. 62/189,918, entitled "Devices and Methods for Anatomic Mapping for Prosthetic Implants," filed Jul. 8, 2015, the disclosure of which is hereby incorporated by reference in its entirety.

BACKGROUND

The embodiments described herein relate generally to prosthetic implants and more particularly, to devices and methods for mapping projected changes in anatomic features resulting from the placement of a prosthetic implant.

Prosthetic devices are often implanted into, for example, diseased portions of a patient to repair, support, stent, and/or otherwise facilitate the proper function of those diseased portions. In some instances, prosthetic devices such as stent grafts can be used to repair diseased portions of a patient's vascular system. For example, aneurysms within a patient's vascular system generally involve the abnormal swelling or dilation of a blood vessel such as an artery, which typically weakens the wall of the blood vessel making it susceptible to rupture. An abdominal aortic aneurysm (AAA) is a common type of aneurysm that poses a serious health threat. A common way to treat AAA and other types of aneurysms is to place an endovascular stent graft in the affected blood vessel such that the stent graft spans across (e.g., traverses) and extends beyond the proximal and distal ends of the diseased portion of the vasculature. The stent graft can thus reline the diseased vasculature, providing an alternate blood conduit that isolates the aneurysm from the high-pressure flow of blood, thereby reducing or eliminating the risk of rupture. In other instances, a prosthetic device can be an implant and/or mechanism, which can provide structural or functional support to a diseased and/or defective portion of the body. In some instances, however, the arrangement of the anatomy can present challenges when attempting to place and/or secure a prosthetic device (including stent grafts or the like). Such challenges can result in misalignment and/or suboptimal configuration of the prosthetic device within the anatomy.

Therefore, a need exists for improved devices and methods for mapping projected changes in anatomic features resulting from the placement of a prosthetic implant.

SUMMARY

Devices and methods for improving the fenestration process of stent grafts are described herein. In some embodiments, a method of generating a patient-specific prosthesis includes receiving anatomic imaging data representative of a portion of a patient's anatomy. A first digital representation of the anatomic imaging data is defined. The first digital representation of the anatomic imaging data is modified. A second digital representation of the portion of the patient's anatomy is defined based on the modifying of the first digital representation of the anatomic imaging data. A patient-specific prosthesis is generated based at least in part on the second digital representation of the anatomic imaging data.

DETAILED DESCRIPTION

Figure 1:
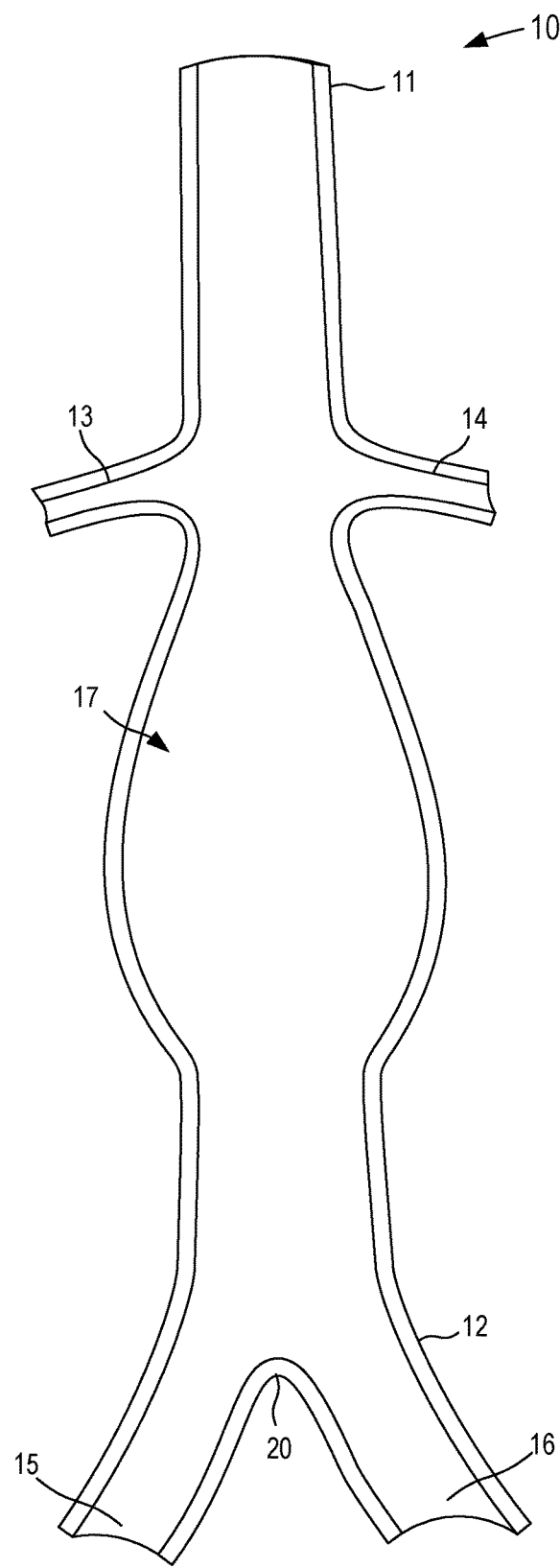
FIG. 1 is an illustration of a diseased abdominal aorta according to an embodiment.

Devices and methods for improving the fenestration process of stent grafts are described herein. In some embodiments, a method of forming a patient-specific prosthesis includes receiving anatomic imaging data representative of a portion of a patient's anatomy. A first digital representation of the anatomic imaging data is defined. The first digital representation of the anatomic imaging data is modified. A second digital representation of the portion of the patient's anatomy is defined based on the modifying of the first digital representation of the anatomic imaging data. A patient-specific prosthesis is formed based at least in part on the second digital representation of the anatomic imaging data.

As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to a direction closer to and away from, respectively, an operator of, for example, a medical device. Thus, for example, the end of the medical device contacting the patient's body would be the distal end of the medical device, while the end opposite the distal end would be the proximal end of the medical device. Similarly, when a device such as an endovascular stent graft is disposed within a portion of the patient, the end of the device closer to the patient's heart would be the proximal end, while the end opposite the proximal end would be the distal end. In other words, the proximal end of such a device can be upstream of the distal end of the device.

The embodiments described herein can be formed or constructed of one or more biocompatible materials. Examples of suitable biocompatible materials include metals, ceramics, or polymers. Examples of suitable metals include pharmaceutical grade stainless steel, gold, titanium, nickel, iron, platinum, tin, chromium, copper, and/or alloys thereof. Examples of polymers include nylons, polyesters, polycarbonates, polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, polyethylene terephthalate (PET), polytetrafluoroethylene (PTFE), and/or blends and copolymers thereof.

The embodiments and methods described herein can be used to form a patient-specific prosthetic device and/or to facilitate the function and/or the integration of the prosthetic device within a portion of a patient. For example, in some embodiments, the devices and/or methods described herein can be used in conjunction with and/or can otherwise be included in endovascular repair using stent grafts. Although the embodiments are shown and described herein as being used, for example, to facilitate endovascular repair, in other embodiments, any of the devices and/or methods described herein can be used to facilitate treatment of any portion of a patient. For example, the devices and methods described herein can form and/or can facilitate the integration of any suitable implant, prosthesis, device, mechanism, machine, and/or the like within a portion of the body of a patient such as the patient's vascular system, nervous system, muscular-skeletal system, etc. Therefore, while the embodiments are shown and described herein as being used in the endovascular repair of an abdominal aortic aneurysm, they are presented by way of example and are not limited thereto.

Some of the devices and/or methods described herein can be used in minimally invasive treatment techniques such as endovascular repair using stent grafts. Such repair techniques are generally preferred over traditional open surgical repair and often result in reduced morbidity or mortality rates. In some instances, however, the arrangement of the diseased vasculature can result in a need to alter a portion of the stent graft prior to insertion into the body. For example, in an endovascular repair of an abdominal aortic aneurysm, the aneurysm can be situated adjacent to and/or directly distal to normally functioning vessels branching from a portion of the aorta. In order to reline the aneurysm with the stent graft, surgeons often cut openings in the stent graft fabric to accommodate specific branch vessel origins, a process known as "fenestration." Specifically, in treating juxtarenal aneurysms, for instance, the fenestrations or openings of the stent grafts can correspond to a size, shape, and/or relative position of, inter alia, the renal arteries.

Traditionally, the fenestration process involves measurements based on medical images (such as CT scans) of the vessel origins. For example, in some instances, longitudinal distances of branch vessels can be measured and relative angular locations of the branch vessels can be estimated and/or calculated from a reference point. Based on these measurements and/or calculations, a surgeon can mark and cut the stent fabric of a stent graft to define one or more fenestrations. The fenestrated stent graft can then be positioned within the diseased vasculature (e.g., via an endovascular procedure) and oriented to substantially align the fenestrations with openings of the corresponding branch vessels.

In some instances, the devices and/or methods described herein can be used to generate and/or otherwise facilitate the formation of a fenestrated stent graft based on medical imaging data of a diseased portion of a patient's vascular system (e.g., an abdominal aortic aneurysm). For example, an electronic device such as a personal computer, workstation, laptop, etc. can receive the imaging data and can calculate and/or otherwise define a digital representation of the imaging data. Based on the digital representation, the electronic device can define one or more templates, process plans, instructions, data sets, and/or the like associated with and/or indicative of a desired set of fenestration locations along a stent graft. In some instances, the electronic device can output a map, plan, and/or template, which in turn, can be used by a doctor, surgeon, technician, and/or manufacturer to form a fenestrated stent graft. For example, in some embodiments, such a template or the like can be substantially similar to those described in U.S. Patent Publication No. 2013/0296998 entitled, "Fenestration Template for Endovascular Repair of Aortic Aneurysms," filed May 1, 2013 ("the '998 publication") and/or those described in U.S. Provisional Patent Application No. 62/151,506 entitled, "Devices and Methods for Anatomic Mapping for Prosthetic Implants," filed Apr. 23, 2015 ("the '506 application"), the disclosures of which are incorporated herein by reference in their entireties.

As described in further detail herein, in other instances, the devices and/or methods described herein can be used to form and/or otherwise facilitate the formation of a fenestrated stent graft without such templates. For example, in some embodiments, the electronic device can output instructions and/or code (e.g., machine code such as G-code or the like) to a computerized numerical control (CNC) device and/or a computer-aided manufacturing (CAM) device, which in turn, can perform one or more manufacturing processes or the like associated with forming and/or otherwise marking fenestration locations along a stent graft. The formation of the patient-specific prosthesis can be performed in a manual process or in at least a partially automated process. Moreover, the devices and/or methods described herein can be used to determine and/or calculate a change in the arrangement of a portion of the anatomy resulting from the insertion and/or indwelling of the prosthesis, and can form a patient-specific prosthesis associated with the portion of the anatomy thereafter, as described in further detail herein.

Figure 2A:
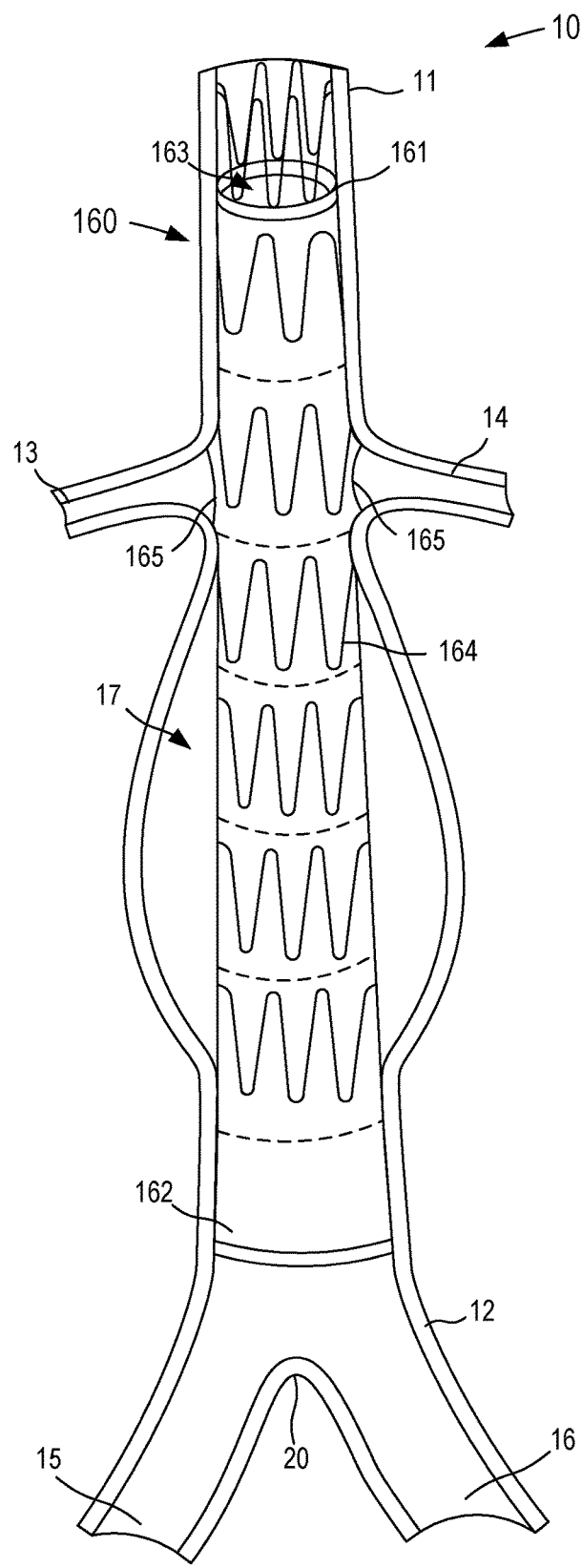
FIG. 2A is a portion of a stent graft according to an embodiment and directly after placement within the diseased abdominal aorta of FIG. 1.
Figure 2B:
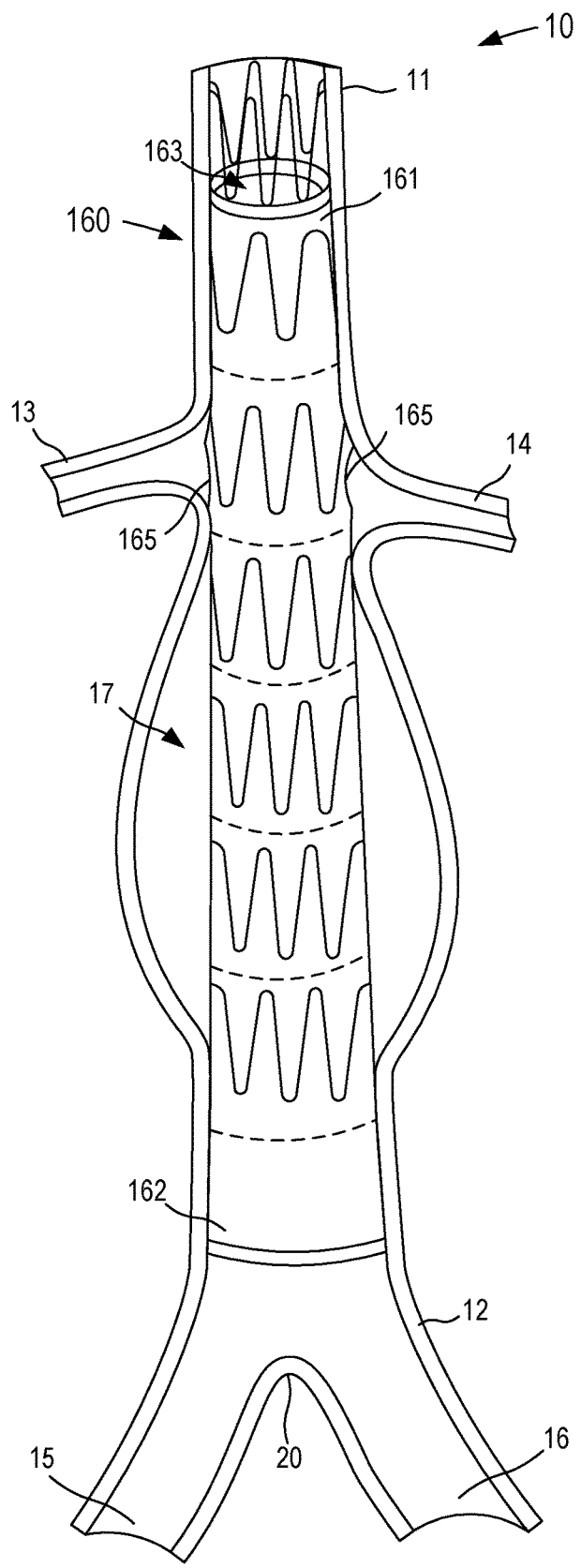
FIG. 2B is a portion of the stent graft of FIG. 2A and placed within the diseased abdominal aorta of FIG. 1 and after a time of indwelling.

FIGS. 1-2B illustrate a diseased portion of a patient's abdominal aorta 10. While portions of the abdominal aorta 10 are described below, the discussion of the abdominal aorta 10 is not exhaustive; rather, the discussion below provides a reference to the relevant anatomic structures. Moreover, the discussion of the anatomic structures (e.g., of the abdominal aorta 10) refers to the position, orientation, etc. of such structures relative to the patient rather than as viewed by an observer (e.g., a doctor). For example, when referring to a "left" side of a patient or to anatomic structures disposed on or near the "left" side of the patient, "left" is intended to describe a position relative to the patient and/or from the patient's perspective, as viewed in an anterior direction (e.g., forward).

The abdominal aorta 10 (also referred to herein as "aorta") has a proximal end portion 11, receiving a flow of blood from the descending aorta (not shown), and a distal end portion 12, supplying a flow of blood to the lower limbs. As shown in FIG. 1, the aorta 10 at or near the proximal end portion 11 supplies a flow of blood to the right renal artery 13 and the left renal artery 14, which in turn, supply blood to the right and left kidney (not shown), respectively. Although not shown in FIG. 1, the proximal end portion 11 of the aorta 10 also supplies a flow of blood to the superior mesenteric artery (SMA) and the celiac artery. The distal end portion 12 of the aorta 10 forms the iliac bifurcation 20, through which the aorta 10 supplies a flow of blood to the right common iliac artery 15 and the left common iliac artery 16, which in turn, supply blood to the right and left lower limbs, respectively. As shown in FIG. 1, this patient has an abdominal aortic aneurysm (AAA) 17 positioned distal to the renal arties 13 and 14 and proximal to the iliac bifurcation 20. More specifically, the AAA 17 is disposed in a position that precludes the attachment of a proximal end portion of a stent graft between the renal arteries 13 and 14 and the AAA 17, and thus, a fenestrated stent graft 160 (see e.g., FIGS. 2A and 2B) is used for endovascular repair of the AAA 17.

In some instances, endovascular repair of the AAA 17 includes scanning and/or otherwise capturing anatomic imaging data associated with the patient's aorta 10. For example, an imaging device can be an X-ray device, a computed tomography (CT) device, a computed axial tomography (CAT) device, a magnetic resonance imaging device (MRI), a magnetic resonance angiogram (MRA) device, a positron emission tomography (PET) device, a single photon emission computed tomography (SPECT) device, an ultrasound device, and/or any other suitable device for imaging a portion of the patient and/or a combination thereof (e.g., a CT/MRA device, a PET/CT device, a SPECT/CT device, etc.). The imaging data captured by the imaging device can thus, be used to determine salient features of the patient's aorta 10 such as, for example, the branch vessels in fluid communication with the aorta 10. For example, a doctor, surgeon, technician, manufacturer, etc. can use the imaging data to determine and/or calculate a size, shape, position, and/or orientation of the aorta 10, the branch vasculature in fluid communication with the aorta 10 (e.g., the renal arteries 13 and 14), and/or any other suitable vasculature or anatomic structure. In some instances, the doctor, surgeon, technician, manufacturer, etc. can form and/or define one or more fenestrations 165 in the stent graft 160 associated with the determined and/or calculated characteristics of at least the renal arteries 13 and 14.

As shown in FIG. 2A, the stent graft 160 can be positioned within a portion of the patient's abdominal aorta 10 via an endovascular procedure. For example, the stent graft 160 can be disposed within a delivery catheter (e.g., in a collapsed, compressed, restrained, and/or otherwise un-deployed configuration), which is inserted into, for example, the femoral artery (not shown). The delivery catheter can be advanced through the artery and into the abdominal aorta 10. Once advanced to a desired position within the abdominal aorta 10, the delivery catheter can be withdrawn relative to the stent graft 160. As the delivery catheter is retracted and/or withdrawn, the stent graft 160 transitions from the collapsed configuration to an expanded or deployed configuration, thereby stenting a portion of the abdominal aorta 10.

The stent graft 160 includes a proximal end portion 161 and a distal end portion 162 and defines a lumen therethrough 163. The stent graft 160 can be any suitable stent graft. For example, the stent graft 160 can be formed from a resilient, biocompatible material such as those described above. For example, a stent graft can include a stent or framework to which a graft material is coupled. In some embodiments, the stent (i.e., framework) can be constructed from a metal or metal alloy such as, for example, nickel titanium (nitinol) and the graft material can be constructed from a woven polymer or fabric such as, for example, polytetrafluoroethylene (PTFE) or polyethylene terephthalate (PET or Dacron®). In some embodiments, the graft material or fabric can be woven onto the stent and/or coupled to the stent in any other suitable manner to form the stent graft (e.g., the stent graft 160).

The stent graft 160 also includes a set of stiffening members 164 disposed circumferentially about the stent graft 160. The stiffening members 164 can be any suitable structure that can, for example, bias the stent graft 160 in an open configuration, thereby structurally supporting the stent graft material (also known as "stent fabric" or "graft fabric"). In some embodiments, the stiffening members 164 can be formed from a metal or a metal alloy such as, for example, those described above. In some embodiments, such a metal or metal alloy, for example, is radiopaque and/or otherwise coated with a radiopaque material configured to be visible using, for example, fluoroscopy. The stiffening members 164 can transition from a restrained or deformed delivery configuration (e.g., when disposed in a delivery catheter) to an expanded and/or biased indwelling configuration, as shown in FIG. 2A.

In this embodiment, the stent graft 160 defines the set of fenestrations 165, as described above. As described herein, the position of the fenestrations 165 along the stent graft 160 can be based on anatomic imaging data and/or one or more digital representations of the patient's anatomy. A doctor, surgeon, technician, and/or manufacturer can then use the imaging data and/or digital representations to define the fenestrations 165 in the graft fabric. As shown, in this example, the fenestrations 165 are each aligned with its corresponding renal artery 13 or 14 and can each have a size, shape, and/or configuration that is associated with its corresponding renal artery 13 or 14. In this manner, the fenestrations 165 can allow blood to flow from the aorta 10 and into the right renal artery 13 and the left renal artery 14 via the fenestrations 165. Although not shown in FIG. 2A, the stent graft 160 can define one or more fenestrations associated with other branch vessels stemming from the aorta 10 such as, for example, the superior mesenteric artery (SMA), the celiac artery, and/or the like.

As shown in FIG. 2B, the placement and/or indwelling of the stent graft 160 within the aorta 10 can, for example, alter, shift, rotate, translate, morph, and/or otherwise reconfigure the arrangement of the patient's aorta 10. As a result, the openings of the renal arteries 13 and 14 are shifted relative to the fenestrations 165 defined by the stent graft 160. In some instances, the shifting of the aorta 10 relative to the stent graft 160 results in at least a partial blockage of the renal arteries 13 and 14, as shown in FIG. 2B. For example, in some instances, the openings of the renal arteries 13 and 14 can be about 4 millimeters (mm) to about 7 mm, and the shifting and/or rearrangement of the aorta 10 can result in a shifting of the openings of the renal arteries 13 and 14 relative to the fenestrations 165 by about 1 mm, about 2 mm, about 3 mm, about 4 mm, about 5 mm, about 6 mm, about 7 mm, or more (or fraction of a millimeter therebetween). Thus, despite defining the fenestrations 165 in desired positions along the stent graft 160 based on the imaging data, the shifting of the aorta 10 resulting from the placement and/or indwelling of the stent graft 160 can result in a blockage of the renal arteries 13 and 14. In some instances, the shifting of the aorta 10 can result in about a 1%, 5%, 10%, 20%, 30%, 40%, 50%, 60%, 70%, 80%, 90%, or 100% (or any percent or fraction of a percent therebetween) blockage of the renal arteries 13 and 14. Although not shown in FIGS. 2A and 2B, the shifting of the aorta 10 can result in a similar misalignment of any branch vessel relative to its corresponding fenestration in the stent graft 160.

In some embodiments, an electronic device can be configured to determine and/or calculate the shift in the anatomy that would result from the insertion and/or indwelling of prosthesis (e.g., a stent graft) and can define one or more digital representations of the shifted anatomy. For example, the electronic device can be a personal computer (PC), a laptop, a workstation, and/or the like disposed in a central location or distributed in multiple locations. The electronic device can include at least a processor and a memory. In some embodiments, the electronic device can also include a display and/or the like. The memory can be, for example, a random access memory (RAM), a memory buffer, a hard drive, a database, an erasable programmable read-only memory (EPROM), an electrically erasable read-only memory (EEPROM), a read-only memory (ROM), a solid-state drive (SSD), and/or the like. The processor can be any suitable processor configured to run and/or execute a set of instructions, for example, stored in the memory. For example, the processor can be a general-purpose processor, a Field Programmable Gate Array (FPGA), an Application Specific Integrated Circuit (ASIC), a Digital Signal Processor (DSP), a central processing unit (CPU), an accelerated processing unit (APU), a front-end processor, a graphics-processing unit (GPU), and/or the like. In some embodiments, the memory can store instructions and/or code to cause the processor to execute modules, processes, and/or functions associated with determining the shift in the anatomy, defining a digital representation of the shifted anatomy, and/or forming one or more fenestrations in a stent graft (e.g., the stent graft 160).

In some embodiments, the digital representation of the shifted anatomy can be a graphical representation of the shifted anatomy that can be presented on the display of the electronic device. In other embodiments, the digital representation of the shifted anatomy can be an instruction, numeric, and/or machine code representation of the shifted anatomy. In still other embodiments, the digital representation of the shifted anatomy can include data associated with a graphical representation and an instruction and/or numeric representation. In addition, the memory can be configured to store data (e.g., in a database) such as imaging data, patient data, data associated with the digital representation of the anatomy and/or shift anatomy, data associated with the prosthesis (e.g., stent graft), data associated with a template or the like, etc., as described in further detail herein.

As described above, the electronic device can receive imaging data of a portion of a patient's anatomy and can determine and/or calculate a change in the portion of the patient's anatomy that can result from the implantation of a prosthetic device. In addition, the electronic device can be configured to define a digital representation of the portion of the patient's anatomy before and/or after the change in the portion of the anatomy. Based on the digital representation of the portion of the patient's anatomy, the electronic device can define, determine, and/or calculate one or more positions along a stent graft each of which is associated with a desired fenestration location in the stent fabric.

For example, an imaging device can be configured to capture and/or scan imaging data associated with a patient's anatomy, as described above. The electronic device can receive the imaging data and can store it in the memory and/or a database included in and/or coupled to the electronic device. For example, the electronic device can be in communication with the imaging device via a wired or wireless network or combination of networks. In other embodiments, a user can cause the imaging data to be saved to the memory and/or the like (e.g., via a user interface such as a universal serial bus (USB) port, a Secure Digital (SD) card reader, a disk drive, and/or the like. Once the electronic device receives the imaging data, the electronic device can perform any number of processes and/or functions associated with analyzing the imaging data to define the digital representation (also referred to herein as "model") of the imaging data. In some embodiments, the electronic device can be configured to present the model of the imaging data on a display and/or the like. In this manner, the electronic device can, for example, graphically represent an accurate anatomic model of the portion of the patient (e.g., the abdominal aorta). In some instances, the electronic device can determine salient anatomic features and can identify them in the model. The electronic device can then define a digital representation that includes only those salient anatomic features, thereby reducing processing load and/or file size. The electronic device can also store any suitable digital representation in the memory and can, for example, associate the digital representations with the patient (e.g., in a database).

In some instances, based on the model of the imaging data, a portion of the model of the imaging data, the model of the salient anatomic features, and/or a combination thereof, the electronic device can define, for example, one or more positions along a stent graft each of which is associated with a desired fenestration location in the stent fabric of a stent graft. Specifically, as described herein, the electronic device can define a digital representation of at least a portion of a stent graft, which includes indications of the desired fenestration locations and/or defines the fenestrations at the desired locations according to the patient's anatomy. In some embodiments, the indications can be, for example, protrusions, markers, frangible portions, and/or any other suitable feature corresponding to, for example, the openings of the aorta leading to the branch vasculature, as described in further detail herein. Although described above as defining a digital representation of at least a portion of the stent graft, in other embodiments, the electronic device can define a fenestration template and/or the like that can be substantially similar to any of those described in the '998 publication and/or the '506 application, incorporated by reference above.

In some instances, the electronic device can also perform one or more processes to adjust, modify, change, update, augment, morph, and/or otherwise alter the data associated with the model to define an updated model based on a set of characteristics associated with at least one of the patient, the prosthesis (e.g., the stent graft), and/or a manner in which the prosthesis will be delivered. For example, as described above, the electronic device can be configured to define an updated model based on the effects of the placement of the prosthesis and its indwelling within, for example, the aorta. Said another way, because the anatomy of at least the abdominal aorta changes when a stent graft is disposed therein and/or while it is being positioned therein, the electronic device is configured to adjust the data associated with the model to account for such changes based on characteristics associated with the patient, the stent graft, and/or the delivery method.

For example, in addition to a mapping (e.g., location information or topography) of the patient's anatomy, the imaging data can also include information related to any other discernable characteristic identified by the imaging technique. Specifically, the imaging data can include, inter alia, a degree of aortic angulation at the juxtarenal neck or other segment of the aorta; a degree, pattern, and location of atherosclerotic disease including plaque, calcification, and/or thrombus; morphometric characteristics of the vascular structure that influence size, position, angulation, or tortuosity such as vessel diameter (i.e., vascular lumen diameter); and/or vessel wall thickness, vessel length, location and number of branch arteries, and/or the like. In some embodiments, the electronic device can extract data associated with these characteristics and can store the extracted data in the memory (and/or a database). Moreover, the extracted data can be stored with and/or otherwise associated with other stored patient data and/or stored prosthetic data. For example, the electronic device can store anthropomorphic data of the patient such as body composition, body temperature, height, weight, body-mass index (BMI), abdominal circumference (absolute or normalized), age, and/or the like; pre-existing vascular or extravascular prostheses or foreign bodies; impact of specific delivery methods such as use of guide wires, catheters, and/or the like; degree of oversizing of the prostheses required to achieve stability; mechanical properties of the prosthesis such as, for example, body material or fabric type, stent or support strut geometry and/or thickness, type of metals or other support materials, stiffness and diameter of the prosthesis and/or devices used to deliver the prosthesis; and/or the like.

In some instances, the electronic device can determine, evaluate, and/or otherwise calculate a weight, value, score, percentage, scale value, influence measure, impact measure, importance measure, and/or any other suitable quantifiable evaluation of the data associated with the aforementioned characteristics. Specifically, the electronic device can perform one or more processes, calculations, evaluations, etc. to determine a quality or measure of impact of the identified characteristics. For example, in some instances, a first amount of angulation of a juxtarenal neck can be greater than a second amount of angulation of a juxtarenal neck. Thus, when a greater angulation of the juxtarenal neck is indicative of and/or otherwise corresponds to a shifting and/or changing of the aortic arrangement resulting from the placement of a stent graft, the first amount of angulation can be associated with a greater value, score, weight, measure, etc., than the second amount of angulation.

Expanding further, in at least one embodiment, the electronic device can perform such an analysis based on, for example, a weighted analysis in which characteristics and/or factors resulting in a greater amount of shifting of the aortic anatomy are associated with a greater amount of weighting than those that affect a lesser amount of shifting. The weighting of the characteristics can be associated with a value (e.g., a multiplier or the like) such as, for example, a percentage represented in decimal format between zero and one (e.g., 10% represented as 0.1, 25% represented as 0.25, 50% represented as 0.5, etc.). In other instances, the percentages used in a weighted analysis can be 100% or greater represented in decimal format (e.g., 125% represented as 1.25, 175% represented as 1.75, 200% represented as 2.0, etc.). In still other instances, the weighted analysis can be based on any suitable scoring system or scale such as, for example, 1-10, 1-100, 1-1000, etc. including whole numbers or fractions thereof.

In some instances, a first set of characteristics can have a greater weight than a second set of characteristics. For example, in some embodiments, the characteristics extracted from the imaging data can, as a group, have a higher weight than the set of characteristics associated with, for example, methods of placing the stent graft, as a group. In this manner, the electronic device can perform any suitable evaluation, calculation, determination, etc. of the set of characteristics associated with the prosthesis (e.g., the stent graft), the patient, and/or the delivery method of the prosthesis. Moreover, while specific examples of a weighting system are described, in other embodiments, the electronic device can perform any suitable weighting and/or evaluating technique. In some embodiments, the characteristics are generally associated with a numerical measure (e.g., a stiffness of the prosthesis is a calculable value based on the properties of the material); thus, the electronic device can be configured to use the "intrinsic" or predetermined values in a predefined equation or the like. Moreover, by quantifying such characteristics, the electronic device can adjust and/or update the data associated with the model to define an updated model based on an anticipated, predicted, predetermined, calculated, and/or otherwise probable shift in the arrangement resulting from the insertion and/or indwelling of the endovascular stent graft. Said another way, the model can be based on a predetermined data set, and the predetermined data set can be updated based on data associated with an anticipated, predicted, predetermined, calculated, and/or otherwise probable shift in the arrangement resulting from the insertion and indwelling of the endovascular stent graft. In some instances, the electronic device can present the updated model on a display or the like.

In some instances, the electronic device can determine a combination of characteristics that lead to a desired (e.g., minimal) amount of anatomic shifting. For example, the electronic device can be configured to perform and/or execute the evaluation, calculation, and/or determination process as described above and can be further configured to iterate through multiple combinations of characteristics associated with the patient, the prosthesis, and/or the delivery method of the prosthesis. As such, the electronic device can determine a combination of characteristics that will result in a smallest amount of anatomic shifting. For example, in some instances, a stent graft having a first amount of stiffness can be associated with a first amount of anatomic shifting, while a stent graft having a second amount of stiffness can be associated with a second amount of anatomic shifting different from the first amount. Thus, based on such an analysis, a doctor, surgeon, technician, and/or the like can select a stent graft having a stiffness that results in a desired amount of anatomic shift (e.g., generally a lesser amount of anatomic shifting), while remaining within, for example, a range of stent graft stiffness that allows for proper treatment.

As described above, based on the updated model of the imaging data, a portion of the updated model of the imaging data, the model of the salient anatomic features and/or an updated model of the salient anatomic features, and/or combination thereof, the electronic device can define, a digital representation, for example, of the stent graft that defines the fenestrations and/or includes indications associated with the fenestrations at the desired locations along the stent graft associated with the projected, anticipated, adjusted, and/or otherwise calculated location of the openings of the aorta leading to the branch vasculature. In some instances, the electronic device can include and/or can be in communication with an output device configured to form and/or output at least a portion of the stent graft. For example, the output device can be a printer, a CNC machine, a CAM machine, and/or the like configured to receive instructions and/or code (e.g., G-code) from the electronic device and to perform one or more processes (e.g., manufacturing processes) associated with forming the stent graft and/or otherwise defining the fenestrations in the stent graft.

Figure 3:
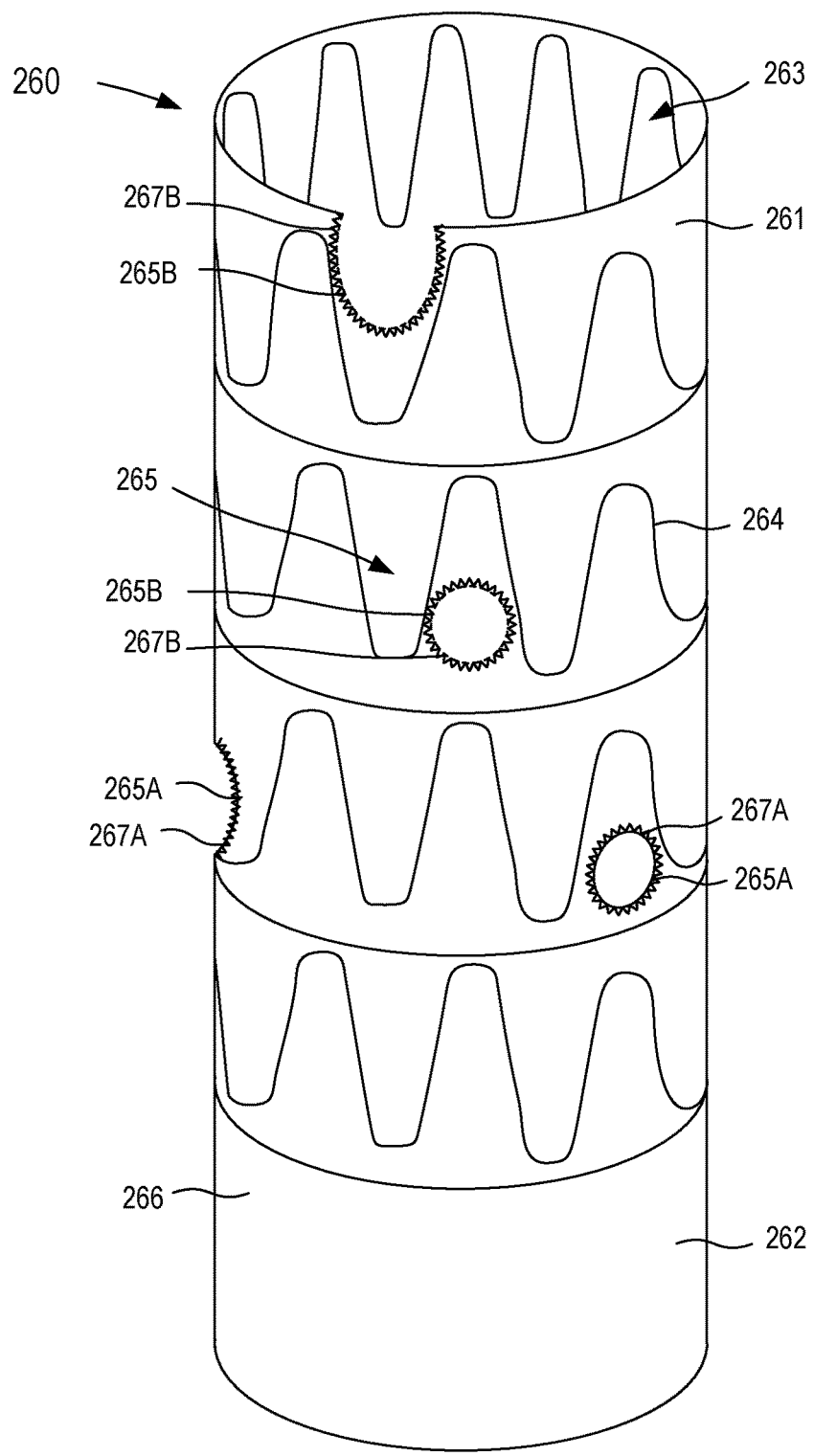
FIG. 3 is an illustration of at least a portion of a fenestrated stent graft according to an embodiment.

FIG. 3 illustrates at least a portion of a fenestrated stent graft 260 according to an embodiment. As described above, a stent graft can define one or more fenestrations configured to accommodate one or more branch vessels when the stent graft is deployed in an aorta. Specifically, in this embodiment, the fenestrated stent graft 260 includes a proximal end portion 261 and a distal end portion 262, and defines a lumen 263 and a set of fenestrations 265. The fenestrated stent graft 260 can be any suitable stent graft and/or prosthesis. For example, in some embodiments, the fenestrated stent graft 260 can be an off-the-shelf stent graft. In other embodiments, the fenestrated stent graft 260 can be a patient-specific stent graft with a size, shape, and/or configuration corresponding to the patient's anatomy.

The fenestrated stent graft 260 (also referred to herein as "stent graft") can have any suitable shape, size, and/or configuration. For example, in some embodiments, the stent graft 260 can have a size that is associated with a size of the lumen defined by the aorta. In other embodiments, the fenestrated stent graft 260 can have a size that is associated with an adjusted or calculated size of the lumen defined by the aorta resulting from the endovascular placement of the stent graft 260. Moreover, the stent graft 260 can have any suitable mechanical properties such as, for example, strength, stiffness, etc.

As shown in FIG. 3, in some embodiments, the stent graft 260 can include stent 264 and a graft fabric 266. The stent 264 can be, for example, any suitable stent and/or framework configured to increase a stiffness of the stent graft 260 and/or to provide structural support for the stent graft 260. As described above, the stent 264 can be formed from any suitable metal or metal alloy such as nitinol. In some embodiments, the stent 264 can be configured to transition between a first, expanded and/or implanted configuration and a second, collapsed, and/or delivery configuration. Furthermore, in some instances, the stent 264 can be biased such that the stent 264 is in the first configuration until a force is exerted on the stent 264 to transition it from the first configuration to the second configuration (e.g., when disposed in a delivery cannula or the like).

The graft fabric 266 can be formed from any suitable polymer or fabric such as, for example, Dacron® or the like. In some embodiments, the graft fabric 266 can be woven around and/or through the stent 264. In other embodiments, the graft fabric 266 can be coupled to the stent 264 via sutures, a friction fit, or an adhesive, and/or can encapsulate the stent 264 between at least two layers of graft fabric 266. As shown in FIG. 3, the graft fabric 266 defines the fenestrations 265, which can be arranged relative to the stent 264 such that the fenestrations 265 do not overlap the stent 264. In other words, the fenestrations 265 can be arranged along the stent graft 260 such that one or more portions of the stent 264 do not span and/or otherwise traverse the fenestrations 265. In other embodiments, one or more portions of the stent 264 can span and/or otherwise traverse the fenestration 265. Moreover, as described in detail above, the fenestrations 265 can be defined by the graft fabric 266 at locations along the stent graft 260 based on an updated, projected, anticipated, and/or otherwise calculated digital representation of a portion of a patient's vasculature.

As described above, the stent graft 260 can be any suitable stent graft and can be formed via any suitable manufacturing process or processes. In some embodiments, the stent graft 260 can be manufactured as an off-the-shelf stent graft and the fenestrations 265 can be formed in the graft material 266 in a subsequent manufacturing process. In other embodiments, the stent graft 260 can be manufactured as a "custom" or not-off-the-shelf stent graft. While specific methods of manufacturing are described herein, it is to be understood that the methods are presented by way of example only and not limitation. Moreover, the methods of manufacturing described herein can be performed at a single facility and/or in a single manufacturing process or can be performed at multiple facilities and/or in multiple manufacturing processes. In some instances, portions of the methods of manufacturing described herein can be performed by an end user such as a doctor, surgeon, technician, nurse, etc. Thus, while the manufacturing of the stent graft 260 is specifically described below, the stent graft 260 can be formed via any suitable manufacturing process or processes and is not limited to those discussed herein.

In some instances, the stent graft 260 can be manufactured with a general shape, diameter, length, etc. associated with a patient's aorta based on, for example, calculations from anatomic imaging data of the patient. In other embodiments, the stent graft 260 can have a general shape, size, and/or configuration associated with the updated model defined by the electronic device, which in turn, corresponds to a calculated, projected, and/or modified arrangement of the aorta in response to the insertion and indwelling of, for example, the stent graft 260, as described in detail above. Hence, a stent graft 260 generally has a tubular or cylindrical shape. In some embodiments, the diameter of the lumen 263 is at least partially based on a diameter of the calculated, projected, and/or modified lumen defined by the aorta. Moreover, the stent graft 260 can have a stiffness and/or any other suitable mechanical properties associated with an anticipated amount and/or method of shifting of the aorta resulting from the insertion and/or indwelling of the stent graft 260, as described in detail above.

The fenestrations 265 are defined along the stent graft 260 such that each fenestration 265 corresponds to a calculated position of the corresponding branch vasculature such as, for example, the renal arteries. In addition, the stent graft 260 defines and/or can optionally define one or more fenestrations 265 corresponding to one of the SMA, the celiac artery, and/or any other branch vasculature. In addition, the diameters of the fenestrations 265 defined by the stent graft 260 can substantially correspond to the actual or calculated diameters of the openings of the branch vessels in fluid communication with a patient's aorta (see e.g., FIG. 4). In other embodiments, the fenestrations 265 can have a predefined diameter, for example, between about 2 mm and about 10 mm. While the stent graft 260 is shown as having four fenestrations 265, the position and/or number of the fenestrations 265 can be arranged in any suitable manner corresponding to the calculated position and/or number, respectively, of the branch openings defined by the patient's aorta. In other words, the size, shape, number, and/or arrangement of the fenestrations 265 defined by the stent graft 260 is based on the calculated, projected, and/or modified digital representation of the patient's aorta resulting from the insertion and/or indwelling of the stent graft 260.

The fenestrations 265 can be formed in the graft fabric 266 in any suitable manner. For example, in some embodiments, the graft fabric 266 can be coupled to and/or woven about the stent graft 260 prior to the formation of the fenestrations 265. For example, in some embodiments, the stent graft 260 can be an off-the-shelf stent graft and the fenestrations 265 can be formed in a subsequent manufacturing process and/or the like. As described above, the electronic device is configured to receive anatomic imaging data of the patient and based on characteristics associated with the patient, the stent graft, and/or the manner of inserting the stent graft, can determine and/or define an adjusted and/or updated digital representation of the patient's anatomy associated with a shifting of the anatomy due to the insertion and/or indwelling of the stent graft 260. In some instances, the electronic device can store data associated with the stent graft 260 in the memory and/or in a database, which in some instances, can include a digital representation and/or model (e.g., CAD or CAM model) of the stent graft 260. As such, the electronic device can also be configured to determine and/or define a digital representation of the stent graft 260 that includes the fenestrations 265 and/or indications of the fenestrations 265 based on data associated with the projected and/or anticipated location and arrangement of the branch vasculature. As described above, the digital representation of the stent graft 260 (including the fenestrations 265) can be a graphical representation, an instruction, number, and/or a code-based representation, or both.

With the digital representation of the stent graft 260 defined, the electronic device can be configured to output data associated with the stent graft 260 and/or with forming the fenestrations in the stent graft 260. For example, in some embodiments, the electronic device can output machine code (e.g., G-code) to a CNC machine and/or CAM machine, which in turn, can receive the output and can perform one or more associated manufacturing processes. For example, in some instances, the electronic device can send instructions to a CNC punch, drill, mill, laser cutter, water jet, and/or any other suitable cutting device. In such instances, the stent graft 260 (e.g., without the fenestrations 265) can be loaded into the machine in an automated, semi-automated, or manual process and can be supported therein such that an overall shape of the stent graft 260 remains substantially constant. For example, a backing plate, or rod, can be inserted through the lumen 263 of the stent graft 260 to substantially maintain the stent graft 260 in the first or expanded configuration. In addition, the stent graft 260 can be oriented globally, locally, or both relative to the machine and the machine, for example, can initialize and/or otherwise register the stent graft 260.

With the stent graft 260 in the desired position and/or orientation and with the machine initialized or the like, the machine can perform one or more manufacturing operations associated with forming the fenestrations 265 in the graft fabric 266 and/or otherwise providing an indication of the fenestrations 265. For example, in some embodiments, the electronic device can output instructions to a CNC punch or the like that can perform a punching operation to define the fenestrations 265 in the graft fabric 266 at the desired and/or calculated locations. Moreover, by positioning, orienting, and/or initializing the machine, the fenestrations 265 can be formed in the graft fabric 266 at positions other than those where the stent 264 is positioned, as shown in FIG. 3. In other embodiments, one or more fenestration 265 can be positioned such that a portion of the stent 264 spans and/or traverses the fenestration 265. In some embodiments, the forming of the fenestration 265 can be such that the portion of the stent 264 is substantially unaffected (e.g., not cut, deformed, bent, severed, etc.). In other embodiments, the forming of the fenestration 265 can include cutting, deforming, and/or removing a portion of the stent 264 that would otherwise traverse the fenestration 265. In some such embodiments, a support structure or the like can be coupled (e.g., via sewing, weaving, an adhesive, etc.) to the stent graft 260 to provide support that would otherwise be provided by the removed portion of the stent 264. Although described as being a CNC punch, in other embodiments, any suitable cutting, punching, puncturing, milling, and/or drilling machine can be used in a substantially similar manner. While described above as forming the fenestrations 265, in other embodiments, a machine can receive the output from the electronic device and in response, can form an indication of the fenestrations 265 on the graft fabric 266. For example, in some embodiments, the machine can be configured to spray and/or otherwise direct paint and/or stain at the locations along the stent graft 260 associated with the fenestrations 265. In such embodiments, the stent graft 260 can be sold and/or shipped with the indications of the fenestrations 265 and an end user (e.g., doctor, surgeon, technician, etc.) can form the fenestrations in the stent graft 260.

In other embodiments, the fenestrations 265 can be formed in a substantially manual manufacturing process (e.g., a process including human intervention). For example, in some embodiments, the electronic device can define the digital representation of the stent graft 260 and can output data associated with the digital representation, for example, to a projection device or the like (e.g., a laser projector). As such, the projection device can receive the output from the electronic device and, in response, can project a visual representation of the stent graft 260, including indications of the fenestrations 265, on a predetermined surface such as a post, rod, mount, etc. In such instances, a manufacturing technician or the like can position the stent graft 260 (e.g., without the fenestrations 265) about the surface and can orient the stent graft 260 to align at least a portion of the stent graft 260 with the projected visual representation of the stent graft 260. For example, although not shown in FIG. 3, the stent graft 260 can include an indicator or the like that can be aligned with a corresponding projected indication. Thus, the projection device can project the visual representation of the stent graft 260 on the physical stent graft 260 and the manufacturing technician can form the fenestrations 265 in the desired locations using any suitable cutting and/or punching device.

Although the manufacturing processes described above have included the graft fabric 266 coupled to the stent 264 in a manufacturing process prior to forming the fenestrations 265, in other embodiments, the fenestrations 265 can be formed in the graft fabric 266 prior to coupling to the stent 264. For example, while the stent graft 260 has a generally cylindrical shape, in some instances, the digital representation of the stent graft 260 (described above) can include data associated with, for example, a flat pattern of the graft fabric 266. That is to say, the electronic device can define data associated with the graft fabric 266 in a substantially flat configuration with the fenestrations 265 positioned along the graft fabric 266 such that when the graft fabric 266 is coupled to the stent 264 (e.g., transitioned to a substantially cylindrical configuration), the fenestrations 265 are disposed in the desired positions associated with the projected, shifted positions of the corresponding branch vasculature. As such, the fenestrations 265 can be formed in the graft fabric 266 by any suitable cutting, punching, drilling, and/or milling operation, in a substantially similar manner as described above. In other embodiments, the graft fabric 266 can be, for example, printed or the like and can define the fenestrations 265 in the desired positions along the graft fabric 266. Moreover, once the fenestrations 265 have been formed in the graft fabric 266, the graft fabric 266 can be disposed about the stent 264. In some instances, the graft fabric 266 can be positioned relative to the stent 264 such that the stent 264 and/or portions thereof do not traverse the fenestrations 265. The graft fabric 266 can then be coupled to the stent 264 (e.g., via an adhesive or the like). In some embodiments, end portions of the graft fabric 266 can include indicia and/or other indicators configured to indicate, for example, a diameter of the stent graft 260 when placed in the cylindrical configuration. That is to say, in some embodiments, the end portions of the graft fabric 266 can overlap by a predetermined amount associated with a desired diameter of the stent graft 260. In some embodiments, the end portions of the graft fabric 266 can be coupled via an adhesive and/or can be sewn together.

In other embodiments, the stent graft 260 can be formed by weaving the graft fabric 266 and the graft fabric 266 can then be attached to the stent 264. In some embodiments, a weaving and/or sewing machine can receive instructions from the electronic device associated with weaving the graft fabric 266 onto the stent 264. In some instances, the instructions can result in the weaving machine defining the fenestrations 265 by not weaving the graft fabric 266 at positions associated with the fenestrations 265. Thus, the fenestrations 265 are formed in the same manufacturing process that otherwise weaves the graft fabric 266.

Figure 4:
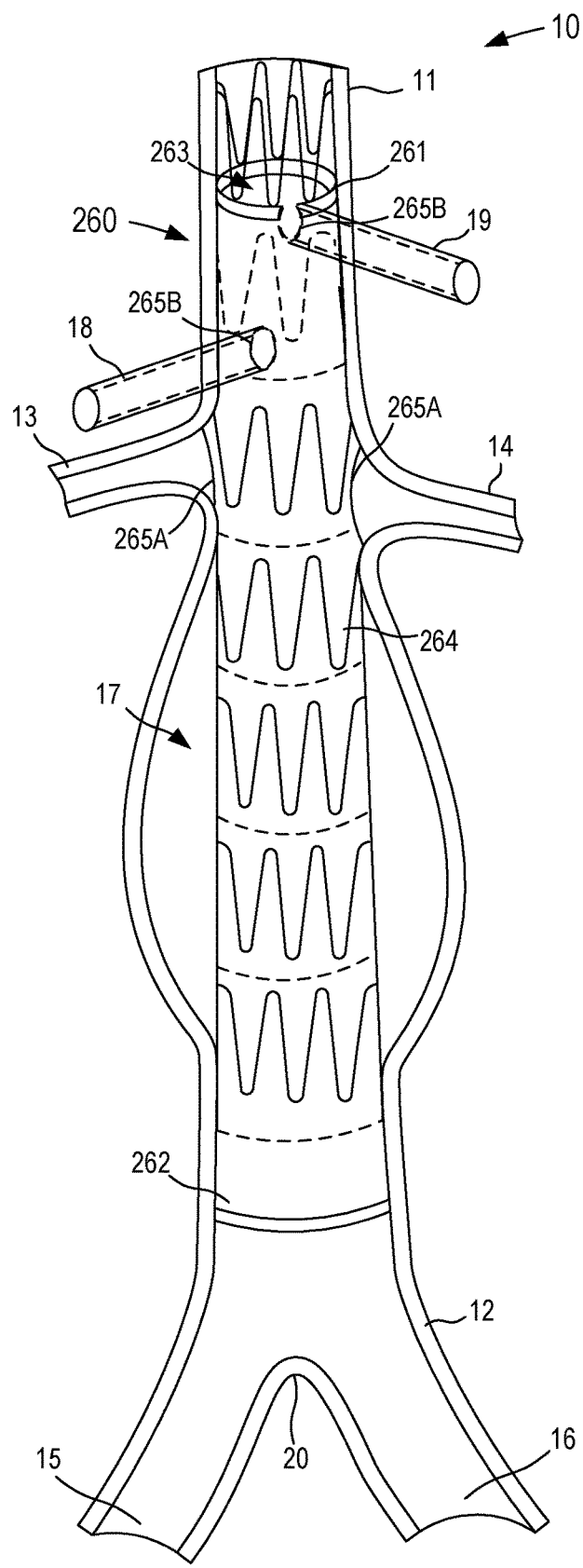
FIG. 4 is an illustration of the portion of the fenestrated stent graft of FIG. 3 positioned, for example, within a portion of a diseased abdominal aorta.

As shown in FIG. 4, when the fenestrations 265 are defined along the stent graft 260, the stent graft 260 can be positioned within a portion of the patient's body using any suitable endovascular procedure. In this embodiment, the stent graft 260 is positioned within the patient's aorta 10. As shown, the stent graft 260 can include, for example, a first set of fenestrations 265A, which are associated with and/or otherwise correspond to the right renal artery 13 and the left renal artery 14. Specifically, each of the fenestrations 265A are aligned with its corresponding renal artery 13 or 14 and can each have a size, shape, and/or configuration that is associated with its corresponding renal artery 13 or 14. In some embodiments, the size, shape, and/or position of the fenestrations 265A is associated with and/or substantially corresponds to the adjusted and/or calculated size, shape, and/or position of its corresponding renal artery 13 and 14. For example, placing the stent graft 260 within the aorta 10 can, for example, alter, shift, rotate, translate, morph, and/or otherwise reconfigure the arrangement of the patient's aorta 10. Thus, by basing the stent graft 260 off of the updated model, the size, shape, and/or position of the fenestrations 265 defined by the stent graft 260 can correspond to the desired branch vasculature (e.g., the right renal artery 13 and/or the left renal artery 14). Moreover, in addition to positioning the stent graft 260 within a portion of the patient's aorta 10, the renal arteries 13 and/or 14 can also be stented, for example, through the fenestrations 265A (not shown in FIG. 4). As such, the stent graft 260 and the stents within the renal arteries 13 and/or 14 can limit and/or substantially prevent migration of the stent graft 260 relative to the patient's aorta 10.

As shown in FIGS. 3 and 4, in some embodiments, the stent graft 260 can include a second set of fenestrations 265B, which are associated with and/or otherwise correspond to other branch vessels that otherwise, might be blocked by an un-fenestrated portion of the stent graft 260. For example, the fenestrations 265B can be associated with and/or otherwise correspond to the superior mesenteric artery (SMA) 18 and the celiac artery 19, respectively. In other embodiments, the stent graft 260 can define fenestrations to accommodate more or fewer branch vessels than illustrated here. For example, in some embodiments, the stent graft 260 can define fenestrations to accommodate the inferior mesenteric artery (IMA), internal iliac arteries, and/or the like. Thus, the fenestrations 265 defined by the stent graft 260 can allow blood to flow from the aorta 10 to the branch vasculature, which would otherwise be obstructed by the stent graft 260 material.

In some embodiments, the arrangement of the stent graft 260 and/or the patient's aorta can be such that a fenestration 265 is partially defined by the stent graft 260. For example, as shown, the proximal most fenestration 265B is disposed at the proximal end of the stent graft 260 and corresponds to the celiac artery 19 that is partially covered by the graft material during deployment. As such, the fenestration 265B for the celiac artery 19 is partially circular or U-shaped to accommodate the portion of the celiac artery 19 otherwise blocked by the graft material. In other embodiments, any of the fenestrations 265 can have non-circular and/or irregular shapes.

In some embodiments, the fenestrations 265 can be marked to facilitate location of the fenestrations 265 during deployment of the stent graft 260. For example, the peripheral edges 267A or 267B of the stent graft 260 that define the fenestrations 265A or 265B may be sutured using gold wires and/or wires of other radiopaque materials. Similarly, the location of the fenestration 265 can be marked by one or more radiopaque markers. Such radiopaque wires or markers can facilitate fluoroscopic visualization of the fenestrations 265 during an endovascular repair procedure and allow a physician to locate the fenestration 265 with respect to the corresponding branch vessel. In other embodiments, the fenestrations 265 can be sutured and/or otherwise marked using any suitable material that can increase visibility, for example, when using any suitable imaging device (e.g., MRI scan, CAT scan, PET scan, X-Ray scan, ultrasound, etc.). Such markers can be placed and/or sutured in any suitable manufacturing process, which can be combined with or separate from the formation of the fenestrations 265.

While the stent grafts 160 and 260 have been described above as being formed via specific manufacturing processes and/or methods, in other embodiments, portions of the stent grafts 160 and/or 260 and, more specifically, the fenestrations 165 and 265, respectively, formed in the stent grafts 160 and 260 can be formed after manufacturing. For example, fenestrations in a stent graft can be formed by a healthcare professional (e.g., a surgeon and/or the like) after delivery of the stent graft. In such embodiments, a kit including any suitable equipment, tool, instruction, pattern, template, etc. can be delivered to, for example, a surgeon with the stent graft or independent of the stent graft. In some instances, such a kit can include, tools and/or equipment used, for example, to mark the location of one or more fenestration on a graft fabric, cut, punch, and/or otherwise form the fenestration, suture any portion of the graft fabric (including suturing radiopaque material (e.g., gold) around the peripheral edge of the graft fabric that defines a fenestration, and/or any other suitable equipment. In some embodiments, the kit can include a fenestration template such as those described in the '998 publication and/or the '506 application, incorporated by reference above. In some embodiments, the kit and/or the components of the kit can be fungible or otherwise disposable (e.g., after one use).

In some embodiments, the arrangement of such a kit can be such that the contents of the kit are stored, sold, and/or delivered in a substantially sterile environment. For example, the kit can be assembled in a substantially sterile environment during a manufacturing process and/or the like and can be sealed such that the components of the kit are in a substantially sterile volume defined by a sealed container or the like. In some instances, the formation of the fenestrations by, for example, the surgeon can be performed in a substantially sterile environment and then can be positioned within the body of the patient. Thus, by maintaining the sterility of the stent graft prior to delivery, the risk of infection and/or complications associated with the patient can be reduced.

The components of the kit can include any suitable tool and/or equipment. For example, in some embodiments, the kit can include a tool that can mark the graft fabric at fenestration locations. The kit can also include a tool that can cut the graft fabric to form the fenestrations (e.g., a scalpel, a knife, a drill (manual or electrically powered), a punch, a laser cutter, and/or any other suitable cutting tool). In some embodiments, the marking tool and the cutting tool can be included in the same device. Moreover, in some embodiments, the kit can include tools configured to form fenestrations having a predetermined size and/or shape, such as, for example, a shape and/or size based at least in part on imaging data of a portion of the patient. By way of example, in some embodiments, a kit can include a cutting tool or bit (e.g., a bit for drilling, punching, burning, etc.), with a predetermined radius or the like, which in turn, can be used to form a fenestration in the graft fabric that has a desired and/or predetermined radius. In some instances, including tools in the kit that are, for example, patient-specific (e.g., predetermined shape and/or size), can reduce a likelihood of error that otherwise could result from misreading and/or misinterpreting imaging data.

In some embodiments, the kit can also include a tool that can couple radiopaque material (e.g., any of those described above) to a portion of the graft fabric surrounding or defining the fenestrations. In some embodiments, such a tool can be a means of suturing the material to the graft fabric such as a suture having one or more radiopaque threads or wires and a suturing needle. In other embodiments, the marking of the fenestrations, the forming of the fenestrations and the coupling of the radiopaque material can be performed using a single tool included in the kit. In some embodiments, the radiopaque markers can be pre-formed (e.g., during a manufacturing process) according to a desired size and/or shape of the fenestrations and coupled to the graft fabric via an adhesive or the like, which can reduce an amount of suturing otherwise performed by a surgeon.

In some embodiments, the kit can include instructions, a template, a model, and/or the like that can facilitate the fenestration process. In this manner, the kit can include any suitable device, tool, equipment, instruction, template, etc. that can increase the efficiency of the fenestration process, can ensure the fenestrations are placed in desired positions, and/or have desired sizes, shapes, and/or arrangements. In some instances, the tools included in the kit can reduce an amount of training and/or skill otherwise desirable for the formation of patient-specific fenestrations. Furthermore, the tools included in the kit can limit and/or substantially prevent damage to the stent graft, resulting from forming the fenestrations, that might otherwise change and/or affect an expected performance of the stent graft (e.g., fixation, sealing, durability, etc.). In some embodiments, the tools included in the kit can be configured to identify and/or mark portions of the graft fabric that are removed from the stent graft (e.g., the cutout portions associated with the fenestrations).

In some embodiments, the tools included in the kit can be compatible with any suitable stent graft. In other embodiments, the kit can be specific to a predetermined stent graft (e.g., manufactured by a specific company and/or according to a size or configuration of the stent graft). In some embodiments, the kit can include the stent graft and any of the tools described above. Moreover, in some embodiments, the kit can include a tool, device, and/or means of placing and maintaining the stent graft in a delivery (e.g., collapsed) configuration. In some embodiments, the kit can include a tool to adjust, alter, and/or reroute the position and/or arrangement of a portion of the stent and/or support strut (e.g., such that the portion of the stent does not traverse a fenestration).

Figure 5:
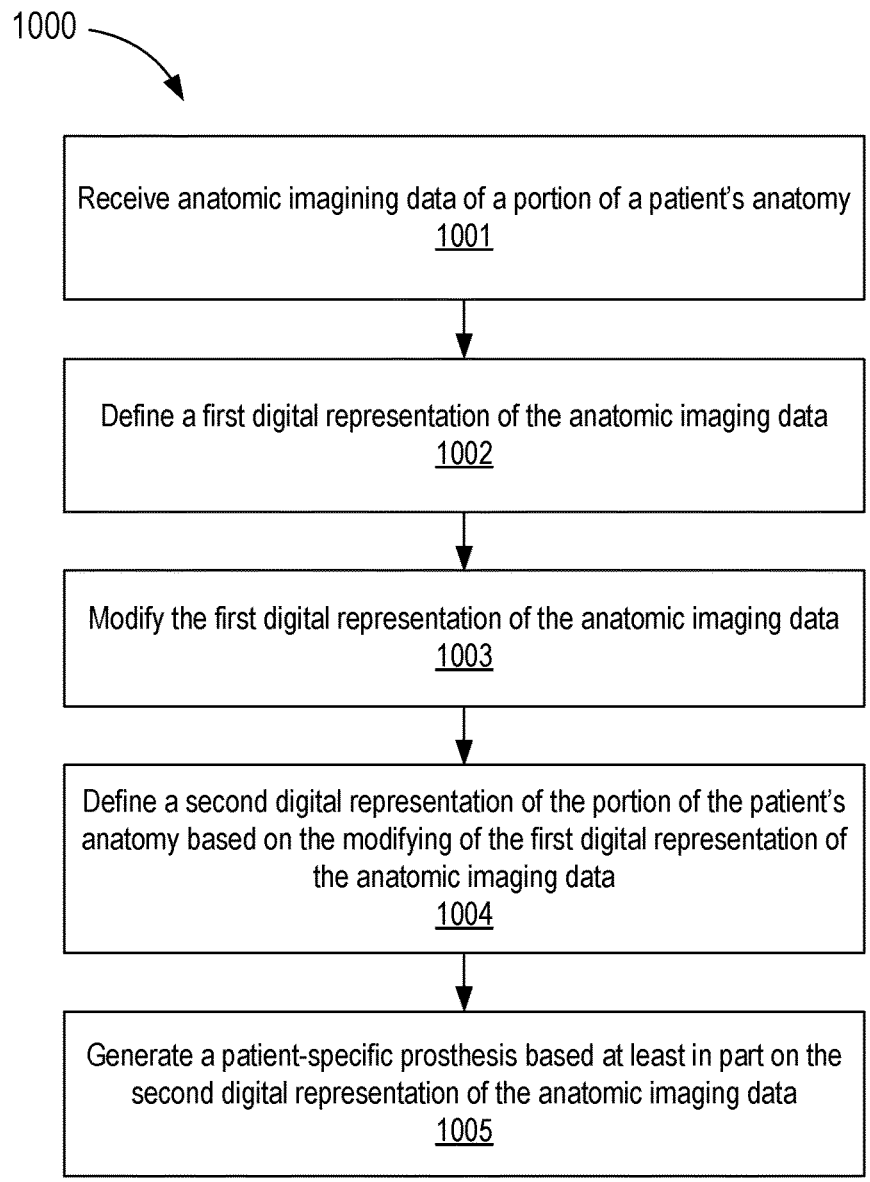
FIG. 5 is a flowchart illustrating a method of forming a prosthetic device, such as a stent graft, according to an embodiment.

Referring now to FIG. 5, a flowchart is presented illustrating a method 1000 of forming a patient-specific prosthesis (e.g., an aortic stent graft) according to an embodiment. The method 1000 includes receiving anatomic imaging data of a portion of a patient's anatomy (e.g., including a blood vessel, such as an abdominal aorta, and/or associated branch blood vessels), at 1001. In some embodiments, an electronic device such as a PC or workstation receives the anatomic imaging data. The electronic device can include a graphic user interface-driven application. The imaging data is from an imaging device in communication with the host device such as, for example, an X-ray device, a computed tomography (CT) device, computed axial tomography (CAT) device) a magnetic resonance imaging device (MRI), a magnetic resonance angiogram (MRA) device, a positron emission tomography (PET) device, a single photon emission computed tomography (SPECT) device, an ultrasound device, and/or any other suitable device for imaging a portion of a patient and/or a combination thereof (e.g., CT/MRA device, PET/CT device, SPECT/CT device, etc.). In some embodiments, the imaging device can scan and/or otherwise capture imaging data of the patient's abdominal aorta and/or a portion thereof.

More specifically, the anatomic imaging data of the portion of the patient's anatomy can be loaded as an input. For example, a user can select and load a DICOM contrast CT series of the patient abdomen. In some embodiments, a variety of images can be loaded, including, for example, computed tomography (CT) images, magnetic resonance (MR) images, and ultrasound (US) images. In some embodiments, two or more images of the same image type or of different image types can be fused to improve image quality, simplify segmentation, and improve measurement accuracy. For example, in some embodiments, different image types (e.g., MR and CT) can be geometrically registered to improve segmentation. Additionally, some features of the portion of the patient's anatomy may be more clearly visible in one image type than another, so fusion of the information from two or more images can improve the clarity and accuracy of the images and/or data.

In some embodiments, data can be resampled for improved image resolution. Data interpolation can be used to improve measurement accuracy. For example, if images are sampled 2 mm apart along the Z-axis, then the point-to-point distance between two images can only be measured in steps of 2 mm. By interpolating between the images (i.e., creating intermediate images between the two), measurement accuracy can be improved. As another example, an additional CT image can be created from two CT images spaced 2 mm apart, such that the additional CT image is placed between the original two CT images and spaced only 1 mm from each of the first two CT images. Data interpolation can improve the accuracy of measurements to, for example, sub-pixel accuracy.

A first digital representation of the anatomic imaging data is defined, at 1002. For example, the electronic device can define the first digital representation or the like associated with and/or corresponding to the patient's anatomy. The first digital representation can be, for example, an anatomic model of the patient's abdominal aorta. In some instances, the first digital representation can be an anatomic model of the patient's abdominal aorta, a first branch blood vessel, and a second branch blood vessel based on the anatomic imaging data. Moreover, in some instances, a user can manipulate the electronic device to cause the anatomic model to be graphically presented on a screen using, for example, a solid modeling program and/or any other computer-aided design (CAD) program.

The images associated with the anatomic imaging data can be displayed such that the user can better visualize the patient's anatomy. The images can be displayed in a standard layout for 3-D medical images. For example, the images can be displayed in a 2×2 layout as axial, sagittal, and coronal slices. The images can also be displayed in a 3-D cube view. In some embodiments, the user can manipulate the images for improved visualization of the anatomy. For example, the user can step through the slices, change contrast settings, and change the zoom settings (i.e., adjust the magnification).

Image processing algorithms can be used to segment the portion of the patient's anatomy (e.g., the aorta) to focus on the volume of interest. After segmentation, the image data can be cropped to speed up image processing. In some embodiments, the volume of interest can be manually entered by a user via a user-selected file or through interactive user input. In other embodiments, the volume of interest can be determined automatically using image analysis techniques. For example, the aorta can be identified in contrast CT images. Image analysis techniques can then be used to automatically detect a particular portion of the aorta, such as the space ranging from the celiac artery to the renal artery to the ileac arteries.

In some embodiments, the image processing methods (i.e., image analysis techniques) can determine a sub-volume of interest for further processing. For example, brightness and/or edge detection can be used to determine the location of a particular portion of a patient's anatomy, such as the location of the abdominal aorta and branch vessels (e.g., the renal artery). The location data of the sub-volume of interest can be used to define the sub-volume of interest such that it contains only the data associated with the sub-volume of interest (e.g., a sub-volume of interest including only the aorta and branch vessels).

In some embodiments, atlas-based methods can be used to model the anatomy to avoid noisy or incomplete data. Such methods begin with the expected layout of the patient's anatomy, such as the relative locations of anatomical features and expected ranges of dimensions. For example, for a typical patient, the celiac artery is expected to be positioned above the renal arties. Additionally, the diameters of the renal arteries are expected to range from about 4 mm to about 10 mm.

In some embodiments, the method can include modifying the initial anatomical model (i.e., the first digital representation) created from the anatomic imaging data using additional data collected through any method described herein. Because the initial anatomical model is used as a starting point and the initial anatomical model is then adjusted with collected data, this method avoids holes in the model that can result from incomplete data. Additionally, noise can be avoided because a user or image processing algorithm can recognize if collected data is within an expected range of the initial anatomical model. If collected data is outside of an expected range, the data can be discarded or flagged for review.

In some embodiments, a combination of user input and automatic detection is used to define the volume of interest. For example, after an initial automatic detection using the methods described herein, user input can be used to refine the boundaries of the volume of interest.

Particular portions of the patient's anatomy, such as the branch vessels of the aorta, can be automatically segmented. In some embodiments, segmentation can be through "region growing." For "region growing" segmentation, initial seed points can be user-specified or automatically detected. Next, additional nearby data points with similar characteristics to the initial seed points can be identified. Similar characteristics can include, for example, intensity values. For example, CT images can be quantified using Hounsfield units. An expected range of Hounsfield units for blood vessels in contrast CT images can be identified. The expected range can be used to identify data points in the CT images that are likely to be associated with blood vessels. The initial seed points and nearby data points with similar characteristics can be combined to create a model of the particular portion of the patient's anatomy, such as the branch vessels. In other embodiments, the particular portion of the patient's anatomy can be automatically segmented using deformable models. For example, the boundary of a vessel can be detected in a first image. The boundary can be, for example, circular or elliptical. The boundary in the first image can be "grown" through the volume of interest (i.e., the boundary shape in the first image can be stacked through the volume). Constraints can be imposed on the overall shape of the "grown" boundary such as, for example, smoothness or orientation. In other embodiments, an atlas-based model can be used to segment the vessel. An initial "atlas" model can be constructed from training data and expert knowledge. Additional data, which may be collected from the patient, can be used to map the initial "atlas" model to the patient's anatomy.

Following segmentation, portions of the patient's anatomy can be extracted from the segmented images. For example, the aortic trunk and the branch vessels can be segmented and extracted. Morphological filters can be used to separately extract the aortic trunk and branch vessels. Alternatively or additionally, in some embodiments, elliptical contours can be fitted to the segmented surface points. Outlier detection methods can then be used to exclude branch vessel points and only fit points that belong to the main trunk.

In some embodiments, each vessel can be identified using a user's knowledge of anatomy and patient orientation (e.g., right versus left). For example, the user can distinguish between the left and right renal arteries and between the celiac artery and the superior mesenteric artery (SMA). Another example is that the user may know the relative locations of vessels in a typical anatomy (e.g., the celiac is above the renal arteries) and the user can use this information in identifying each vessel. A third example is that the user may intend to identify a portion of the aorta with a specific shape (e.g., a long tube with four to six branch vessels). Each of the dimensions of the specific shape can have an expected range of values (e.g., the aorta diameter will be between 15 mm and 30 mm). Thus, knowledge of the anatomy can assist with segmentation and locating, for example, an aneurysm. Additionally, relevant information from the patient's medical record (e.g., a missing renal artery) can be used.

In some embodiments, centerlines of portions of a patient's anatomy can be extracted from the segmented portions. For example, the centerlines of the aortic trunk and branch vessels (i.e. the lines passing through the central axes of the aortic trunk and branch vessels and following the geometry of the main trunk and branch vessels) can be extracted from the segmented portions of the aortic trunk and branch vessels. In some embodiments, the centerlines can be extracted automatically. In some embodiments, a curved planar reformation (CPR) image can be optionally generated and displayed. In some embodiments, a distance transform can be applied to a segmented image and can connect points with maximum distances using a fast marching method. The distance transform allows for distances from each point in the segmented image to the closest neighbor of each point in the background to be computed. For example, if the distance transform is applied to a circular contour the distances will be maximum at the center and decrease radially. A fast marching method can then be applied to connect points with maximum distances. In other embodiments, contours (e.g., elliptical, spline, etc.) can be fit to the segmented image and centroids or weighted centroids of the contours can be computed to define the centerline. In other embodiments, vessel specific properties can be computed and used to compute centerlines. For example, vesselness, a measure of how similar a structure is to tube used in some methods of image segmentation, can be computed and used to compute centerlines.

The first digital representation of the anatomic imaging data is modified, at 1003. For example, as described above, the patient's anatomy can shift, rearrange, and/or otherwise adjust when a prosthetic implant or device such as an endovascular stent graft is disposed therein. When the portion of the patient's anatomy is a portion of the abdominal aorta, this shifting can result in a corresponding shifting or movement of the openings to the branch vasculature in fluid communication with the aorta, which in turn, can result in a reduction in accuracy of the first digital representation of the anatomic imaging data relative to the shifted anatomy. Accordingly, in some embodiments, the electronic device can adjust and/or update data associated with the first digital representation.

For example, the data can be adjusted and/or updated based on patient data such as a degree of aortic angulation at the juxtarenal neck or other segment of the aorta; a degree, pattern, and location of atherosclerotic disease including plaque, calcification, and/or thrombus; morphometric characteristics of the vascular structure that influence size, position, angulation, or tortuosity such as vessel diameter (i.e., vascular lumen diameter); and/or vessel wall thickness, vessel length, location and number of branch arteries, and/or the like; anthropomorphic data of the patient such as body composition, body temperature, height, weight, BMI, abdominal circumference (absolute or normalized), age, and/or the like; pre-existing vascular or extravascular prostheses or foreign bodies, and/or the like. In some instances, the data can be adjusted and/or updated based on data associated with mechanical properties of the prosthesis such as, for example, body material or fabric type, stent or support strut geometry and/or thickness, type of metals or other support materials, stiffness and diameter of the prosthesis, an amount of oversizing of the prosthesis, and/or the like. In addition, the data can be adjusted and/or updated based on data associated with a delivery method of the prosthesis such as, for example, an impact of specific delivery methods such as use of guide wires, catheters, and/or the like. A second digital representation of the portion of the patient's anatomy is defined based on the modifying of the first digital representation of the anatomic imaging data, at 1004. In other words, the first digital representation of anatomic imaging data can be associated with a portion of the patient's anatomy in a first configuration and a second digital representation of the anatomic imaging data can be associated with the portion of the patient's anatomy in a second configuration. The portion of the patient's anatomy can transition from the first configuration to the second configuration in response to insertion of a prosthetic (e.g. a patient-specific prosthetic).

In some embodiments, the first digital representation of anatomic imaging data can be modified based on a predetermined data set, and the predetermined data set can be based on data associated with the second digital representation. By quantifying characteristics of, for example, a patient-specific prosthetic, a patient, and/or a manner of introducing the patient-specific prosthetic to a portion of a patient's anatomy, the data associated with the first digital representation can be adjusted and/or updated to define the second digital representation based on an anticipated, predicted, predetermined, calculated, and/or otherwise probable shift in the arrangement resulting from the insertion and indwelling of a prosthetic (e.g., an endovascular stent graft). Said another way, the first digital representation can be based on a predetermined data set, and the predetermined data set can be updated based on data associated with an anticipated, predicted, predetermined, calculated, and/or otherwise probable shift in the arrangement resulting from the insertion and indwelling of the prosthetic.

In some embodiments, the anatomic imaging data can be a first anatomic imaging data set. The modifying of the first digital representation of the first anatomic imaging data set can be based on data associated with the patient-specific prosthetic, a patient, and/or a manner of introducing the patient-specific prosthetic to a portion of a patient's anatomy. The data associated with the patient-specific prosthetic, a patient, and/or a manner of introducing the patient-specific prosthetic to a portion of a patient's anatomy can be updated with data associated with a second anatomic imaging data set, the second anatomic imaging data set being representative of the patient-specific prosthetic disposed within the portion of the patient's anatomy.

Specifically, in some embodiments, the modification of the first digital representation to define a second digital representation of the portion of the patient's anatomy (i.e. the predicted changes in the patient's anatomy) can be based on predicted changes to the centerline of a portion of the patient's anatomy. For example, the modification can be based on predicted changes to the extracted centerline of the aortic trunk. The extracted centerline (as described above) is typically a sequence of points in 3-D space (e.g., having x-, y-, and z-coordinates). A low order polynomial function can be fitted to the points using a least squares fitting technique to produce a modified centerline (i.e., an adjusted centerline) that is a prediction of the shape of the portion of the patient's anatomy after insertion of a graft.

In some embodiments, the modification of the first digital representation to define a second digital representation of the portion of the patient's anatomy (i.e. the predicted changes in the patient's anatomy) can be based on the expected deformation of the patient's anatomy as a result of inserting a device (e.g., a graft) into the anatomy. For example, mathematical models of the segmented volumes and/or surfaces, such as finite element method (FEM) or parametric representations, can be created based on expected deformation of the segmented volumes and/or surfaces. Models reflecting the expected deformation can be built from training data consisting of pre-procedure, intra-procedure, and post-procedure images. The anatomy of interest can be segmented and the resulting changes can be modeled using machine learning approaches. In other words, data can be collected from a deformed portion of one or more patients' anatomy (e.g., a deformed aorta) and the data can be used to create a training data set. The training data set can be used to model the predicted deformation of a portion of a patient's anatomy in future procedures.

In some embodiments, the modification of the first digital representation to define a second digital representation of the portion of the patient's anatomy can take into account characteristics of a particular device (e.g., a patient-specific prosthetic) to be delivered to the anatomy. For example, the modification can take into account the wire stiffness of a graft and account for variations in wire stiffness between manufacturers. In some embodiments, for example, a lower order polynomial fit can be used to model the predicted change in centerline if a stiffer device is inserted into the anatomy (e.g. a stiffer graft). Additionally, training data can be used to model changes as a result of the characteristics of particular devices.

In some embodiments, the modification of the first digital representation to define a second digital representation can take into account anatomic-specific information (e.g., characteristics associated with a specific patient or set of patients). For example, if the particular patient's anatomy is unusually angulated, the anatomical shift of the anatomy as a result of a device being inserted (e.g., a graft) is likely to favor one side of the anatomy (e.g. the aorta vessel wall). Additionally, the insertion location (e.g., left versus right femoral artery) can cause the device to favor one side of the anatomy (e.g. aorta vessel wall). Training data can also be used to model changes as a result of a particular patient's anatomy. Additionally, in some embodiments, the modification of the first digital representation to define a second digital representation can take into account procedure-specific details (i.e., characteristics associated with a method of introducing a patient-specific prosthetic to the anatomy). For example, the modification can account for insertion location (e.g., left side versus right side), patient breathing, and/or physician preferences.

In some embodiments, the user (e.g., clinician or surgeon) can manually account for patient-specific details (i.e., characteristics associated with a patient). For example, a user can use a different method to locate (for digitally representation) the distal or proximal end of a vessel depending on the presence of a calcium deposit. In other embodiments, the modification of the first digital representation can take into account patient-specific details using algorithms. For example, the modification can account for calcium deposits or plaque, the presence of artifacts obstructing blood flow through the aorta, and/or the angle of curvature of the aorta and branch vessels.

In some embodiments, intra-procedure data can be incorporated to refine algorithms used to modify the first digital representation. The intra-procedure data can include imaging data such as fluoroscopy, CT, or any other suitable imaging data. Additionally, in some embodiments, machine learning can be used to refine the algorithms. In some embodiments, intra-procedural data can be used to validate measurements and refine the algorithms. A model (e.g., a modified digital representation) can first be used to predict changes in the anatomy or how the graft would line up along the centerlines of the anatomy. The intra-procedure data can then be analyzed to observe the actual changes. The deviations from the predicted changes to the actual changes (obtained from intra-procedure data) can in turn be used to refine future models (e.g., future digital representations).

For example, patient breathing can deform organs in a non-rigid manner. To account for non-rigid movements, a non-rigid deformation can be applied to pre-operative models (e.g., a first digital representation). The non-rigid deformation can reflect the amount and shape of deformation resulting from a force or forces on a graft caused by patient breathing. Intra-procedure images of a patient can be analyzed and compared to the patient's pre-operative images to determine the appropriate non-rigid deformation for future digital representations.

As another example, intra-procedure images can be used to modify the first representation (i.e. to build a predictive model) based on where the device (e.g. a graft) is expected to eventually be located in the patient based on the side of insertion. For example, grafts that are inserted from the right side of a patient may typically shift to a position next to the left side of the aorta wall. The expected location can be quantified through intra-operative measurements and a predictive model can be created.

Calcium deposits along the arterial wall of a vessel can affect the stiffness of the vessel. Additionally, other calcium deposits and/or diseased portions of the vessel can increase or decrease the stiffness of the arterial wall. Stiffness of the vessel wall is inversely related to the amount of flexibility of the vessel wall. In some embodiments, calcium deposits and/or diseased portions can be accounted for during the modification of the first digital representation pre-operatively by modeling the stiffness as a material property. For example, finite element models can be used that model the stiffness as a material property.

When calcium deposits are located near branch vessels, identification of the location of the branch vessels can be more difficult. In some embodiments, expert clinician knowledge regarding the location of calcium deposits and/or branch vessels can be incorporated into the modification of the first digital representation to define a second digital representation. Clinician inputs can be collected and used to modify the first digital representation (i.e., built into a predictive model) that can be applied to future patients and/or procedures. As the number of patients in a training set increases, the accuracy of the predictive model can increase. Additionally, as more data is collected via the training set, outlier patient data can be discarded.

In some embodiments, portions of the first digital representation can be modified to define the second digital representation using a centerline modified for the second digital representation as described above (i.e. an adjusted centerline). For example, the branch vessel locations (i.e., expected locations of the branch vessels during the procedure) can be predicted using the adjusted centerline of an aorta. As described above, the adjusted centerline can be used to predict the path that the graft will take within a patient's anatomy. The adjusted branch vessel locations can then be predicted by projecting the vessel endpoints (i.e., the points where the vessels join the aorta which can be obtained from imaging data) on to the adjusted centerline of the aorta. Identification of the branch vessel endpoints (proximal and distal ends) can be performed automatically or manually. To identify the branch vessel endpoints automatically, a segmented vessel surface and a segmented aorta surface can be produced using the segmentation steps described above. The intersection points of the segmented vessel surface and the segmented aorta surface can then be used to locate and define the branch vessel endpoints (i.e., where the branch vessel connects to the aorta).

In other embodiments, vessel locations can be predicted by projecting a central point of the vessel along the adjusted centerline of the aorta. The identification of the central point of the branch vessels can be performed automatically or manually. To identify the central point of the branch vessel automatically, the centerlines for the branch vessels, the main centerline of the aorta, and the segmented aorta produced by the segmentation steps above can be used to determine the junction point (also referred to as the "branch vessel junction") where a branch vessel centerline and an outer surface or wall of the segmented aorta intersect (i.e. the central point of the vessel along the outer surface of the aorta based on the adjusted centerline of the aorta). The vessel radius can then be estimated and the vessel location can be defined as ± the radius from the projected branch vessel junction (i.e. the vessel central point on the outer surface of the segmented aorta).

In some embodiments, pre-operative images can be deformed (i.e. the first digital representation can be modified to define the second digital representation) using a deformation field. The deformation field can be created using the output from the finite element models described above for deforming the aorta and associated branch vessels. The output from the finite element models is a deformation field with x, y, and z displacement values for every voxel in the 3-D image. The deformation field can then be applied to pre-operative images to deform them the images will reflect the predicted change in shape of the patient's anatomy as a result of device insertion. Thus, a user (e.g. a clinician or a surgeon) can use the deformed images in accounting for deformations during pre-procedure planning. Additionally, the deformed images can be used as a training tool for surgical residents to aid in learning about intra-operative changes to the shape of the aorta, centerline adjustment, and the like.

In some embodiments, centerlines (e.g., centerlines of the aortic trunk and branch vessels) can be extracted automatically from mathematical models. Said another way, centerlines can be extracted (using methods described herein) from deformed images. In such embodiments, centerlines can be extracted from intra-procedure or post-procedure image data reflecting anatomy deformed by device insertion. Branch vessel locations can then be predicted based on the extracted centerlines. Similarly as described above, these centerlines can be used for pre-procedure planning (e.g. modification of the first digital representation to define a second digital representation) and for training/teaching aids.

A patient-specific prosthetic device is generated based, at least in part, on the second digital representation of the anatomic imaging data, at 1005. For example, as described above, the electronic device can include and/or can send a signal to an output device such as any of the manufacturing device described herein, which in turn, can perform one or more manufacturing processes to generate the patient-specific prosthetic device associated with the updated, adjusted, calculated, and/or otherwise modified data (e.g., the second digital representation), which in turn, is associated with a projected (i.e., predicted), anticipated, and/or calculated arrangement of the patient's abdominal aorta. Specifically, in some embodiments, such a manufacturing device can be configured to form one or more fenestrations in a graft fabric, each of which is associated with a position corresponding to a modified and/or shifted position of a branch vessel of the aorta resulting from the placement of the stent graft, as described in detail above with reference to the patient-specific stent grafts 160 and 260. Thus, the patient-specific prosthetic device can include openings (fenestrations) corresponding to, for example, the openings of the aorta leading to the branch vasculature, as described above with reference to, for example, the patient-specific stent grafts 160 and 260. For example, the patient-specific prosthetic device can include a first fenestration or indicator corresponding to the location of a first branch blood vessel extending from a patient's aorta in the second digital representation and a second fenestration or indicator corresponding to the location of a second branch blood vessel extending from a patient's aorta in the second digital representation.

In some embodiments, the relative locations of the vessels can be automatically quantified in a 3-D or 4-D coordinate system. Additionally, relevant dimensions such as, for example, diameters and volume of flow, can be automatically quantified. This information can be used to modify the first digital representation to define the second digital representation of the portion of the patient's anatomy. The second digital representation can then be used to create a patient-specific prosthetic device (for example, a patient-specific stent graft). For example, the second digital representation can be used to create fenestrations in a stent graft at the predicted location of the vessels such that fenestrations are at the appropriate location and of an appropriate size and shape to allow pass-through of the vessels.

In some embodiments, for example, a graft fabric of the stent graft can be a flat sheet configured to be coupled to a stent of the stent graft (transitioned to a substantially cylindrical configuration). For example, while the stent graft has a generally cylindrical shape, in some instances, the digital representation of the stent graft (described above) can include data associated with, for example, a flat pattern of the graft fabric. That is to say, the second digital representation can define data associated with the graft fabric in a substantially flat configuration with the fenestrations positioned along the graft fabric such that when the graft fabric is coupled to the stent graft (e.g., transitioned to a substantially cylindrical configuration), the fenestrations are disposed in the desired positions associated with the projected, shifted positions of the corresponding branch vasculature. Alternatively, in some embodiments, the second digital representation data can directly feed into the graft manufacturing process to produce a fenestrated graft.

In some embodiments, to form a patient-specific prosthetic device for a portion of a patient's aorta, the average diameter of the aorta at user-specified end points at the celiac and SMA branch vessels can be computed. Next, the locations of the branch vessels can be translated to cylindrical coordinates on the surface of a cylinder. The cylinder can have a diameter equal to the average diameter of the aorta (e.g., the average of the diameter at the celiac and the SMA branch vessels). Each branch vessel location can be defined by its central point and radius on the surface of this cylinder as described above.

In some embodiments, clinical knowledge can be incorporated into the process of quantifying the relative location of vessels. Clinical knowledge can be incorporated automatically or manually. For example, information regarding when to block an accessory vessel, when to create a larger fenestration for multiple vessels, how to account for stenosis, visible calcium buildup, and the like, can be used to modify the patient-specific prosthetic device (e.g., stent graft) based on the second digital representation. In some embodiments, for example, an option can be provided to allow the user to either create a fenestration in the patient-specific prosthetic device (e.g., stent graft) for an accessory renal artery or to block off the accessory renal artery and not provide access through the patient-specific prosthetic device in that location.

In some embodiments, graft manufacturer data, such as CAD models and strut patterns, can be incorporated into the second digital representation and/or the patient-specific prosthetic device. For example, manufacturer strut pattern information can be used to define fenestrations in locations on a graft without struts. In some embodiments, the graft manufacturing process can be modified such that the strut patterns are customized to not overlap with fenestration locations.

Some of the embodiments described herein are configured to define a first digital representation of anatomic imaging data of a portion of a patient's anatomy and to modify the first digital representation to define a second digital representation of the portion of the patient's anatomy based on a set of characteristics associated with the patient, a prosthesis, and/or a manner of delivering the prosthesis. In other embodiments, the second digital representation of the portion of the patient's anatomy can be from a plurality of digital representations of the portion of patient's anatomy. That is to say, in some embodiments, the modifying of the first digital representation of the portion of the patient's anatomy can result in a plurality of modified digital representations of the portion of the patient's anatomy (including the second digital representation). In such instances, each modified digital representation of the portion of the patient's anatomy (simply referred to herein as "modified representation") can be based on a different set of characteristics or a different combination of the characteristics associated with the patient, the prosthesis, and/or the manner of delivering the prosthesis.

For example, a first digital representation of a portion of a patient's anatomy can be modified to define a second digital representation of the portion of the patient's anatomy based on patient data, prosthetic data, and/or a first method of delivering the prosthesis. Similarly, the first digital representation of the portion of the patient's anatomy can be modified to define a third digital representation of the portion of the patient's anatomy based on the patient data, the prosthetic data, and/or a second method of delivering the prosthesis. In this manner, a patient-specific prosthetic device (e.g., the fenestrated stent grafts 160 and 260) based on the second digital representation can also be specific to the first method of delivering the prosthesis, while a patient-specific prosthetic device based on the third digital representation can also be specific to the second method of delivering the prosthesis. In a similar manner, a digital representation can also be based on the size, shape, and/or configuration of the prosthesis. As such, a user can input a selection or the like of a digital representation of a specific prosthetic device from a plurality of specific prosthetic devices. Moreover, in some instances, a score, confidence value, rating, and/or any other indicator can be associated with the digital representation of each prosthetic device and can be indicative of an accuracy of the digital representation of each prosthetic device and the associated modified representation of the patient's anatomy. Said another way, a digital representation of a plurality of patient-specific prosthetic devices and a plurality of confidence values can be defined. Each confidence value from the plurality of confidence values can be associated with the digital representation of a different patient-specific prosthetic device from the plurality of patient-specific prosthetic devices and can represent a degree of accuracy between the digital representation of that patient-specific prosthetic device and the second digital representation of the anatomic imaging data. Thus, in some instances, a user can select a digital representation of the prosthetic device with the highest score suitable for a patient.

Any of the embodiments described herein can be configured to define a modified representation of a portion of a patient's anatomy based on data associated with any suitable set of characteristics associated with the patient, a prosthetic device, a manner of delivery, and/or the like. In some embodiments, the data associated with the set of characteristics can be updated based on, for example, empirical data and/or the like. For example, in some embodiments, a value, weight, score, factor, and/or the like can be associated with each characteristic in the set of characteristics. In some instances, anatomic imaging data can be taken of the portion of the patient's anatomy after the delivery of a prosthesis and based on data included in the post-delivery anatomic imaging data the value, weight, score, factor, and/or the like associated with the set of characteristics can be updated. In this manner, the accuracy of a projected change in the portion of the anatomy resulting from the delivery and/or indwelling of a prosthetic device can be increased based on adjusting and/or "tuning" the weight and/or influence of one or more characteristics associated with the patient, the prosthesis, and/or the delivery method.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Some embodiments and/or methods described herein can be performed by software (executed on hardware), hardware, or a combination thereof. Hardware modules may include, for example, a general-purpose processor, a field programmable gate array (FPGA), and/or an application specific integrated circuit (ASIC). Software modules (executed on hardware) can be expressed in a variety of software languages (e.g., computer code), including C, C++, Java™, Ruby, Visual Basic™, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. For example, embodiments may be implemented using imperative programming languages (e.g., C, FORTRAN, etc.), functional programming languages (Haskell, Erlang, etc.), logical programming languages (e.g., Prolog), object-oriented programming languages (e.g., Java, C++, etc.), numerical control programing languages (e.g., G-code) or other suitable programming languages and/or development tools. Additional examples of computer code include, but are not limited to, control signals, encrypted code, and compressed code.

Some embodiments and/or methods described herein can be performed by software (executed on hardware), hardware, or a combination thereof and configured to process and/or execute one or more programs and/or instructions stored, for example, in memory. Specifically, some of the embodiments described can be configured to process and/or execute one or more programs associated with 3-D solid modeling, computer aided design (CAD), volume or surface reconstruction, image analysis and/or segmentation, and/or the like. Such programs can include but are not limited to, for example, MATLAB, TeraRecon, FreeCAD, SolidWorks, AutoCAD, Creo, and/or the like. Such programs can be used, for example, to identify features of interest, which can be traced with spline curves fit to user-specified points. In addition, indicators or markers can be placed at specific 3-D locations to indicate the origins of the branch vessels. In an embodiment, outlines of the various features or interest and/or origins or branch vessels can be converted to 3-D contours that define the feature locations in the 3-D space. The 3-D contours can be converted to a mesh to define a 3-D surface model. In some embodiments, segmentation software can be configured to obtain different types of imaging data such as CT imaging data, ultrasound data, and/or the like. In some embodiments, the size of the generated 3-D surface model can be modified to optimize the graft fenestration process. For example, the surface model may be radially expanded to add a predefined wall thickness to allow generation of a patient-specific prosthesis, such as a fenestrated endograft.

In some embodiments, such programs can produce 3-D and multi-planar views of CT image sets. In some embodiments, such a visualization tool can perform automatic vessel boundary detection, which can be imported into segmentation software that generates the 3-D surfaces to expedite the model generation and hence the fenestration generation process. In some embodiments, such visualization tools can automatically generate 3-D surface data for a digital model and/or a patient-specific prosthesis, such as a fenestrated endograft. Once the vessel boundaries are identified, corresponding openings in the 3-D digital model can be created and/or defined. In some embodiments, a subtraction between the solid part model and a cylinder with the desired fenestration diameter can define the openings in the 3-D digital model. In another embodiment, holes representing the origins of branch vessels may be added using a CAD program such as those listed above. In some embodiments, a 3-D digital model is converted to a solid object model format such as stereolithography (STL) or Virtual Reality Modeling Language (VRML) that is supported by a 3-D printer or similar patient-specific prosthesis generation device. Advantageously, the availability of automatic aorta boundary detection makes the creation of a patient-specific prosthesis, such as a fenestrated endograft, a practical option for routine use in endovascular aortic aneurysm repair. Raw imaging data or the segmented aorta boundaries and fenestration locations can be sent to an outside processing facility, and the patient-specific prosthesis can be shipped back to the surgery site. Therefore, individual clinical sites need not employ individuals with expertise in image segmentation, CAD software, and/or 3-D output devices.

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made. Although various embodiments have been described as having particular features and/or combinations of components, other embodiments are possible having a combination of any features and/or components from any of embodiments as discussed above.

Where methods and/or events described above indicate certain events and/or procedures occurring in certain order, the ordering of certain events and/or procedures may be modified. Additionally, certain events and/or procedures may be performed concurrently in a parallel process when possible, as well as performed sequentially as described above.

What is claimed:

1. A method, comprising:
   receiving anatomic imaging data representative of a portion of a patient's blood vessel;
   defining a first digital representation of the anatomic imaging data, the first digital representation including data representative of a first location of an anatomic feature of the patient's blood vessel;
   modifying the first digital representation of the anatomic imaging data to generate a second digital representation of the portion of the patient's blood vessel, the second digital representation including data representative of a second location of the anatomic feature of the patient's blood vessel, the second location different than the first location; and
   generating a patient-specific prosthesis based at least in part on the second digital representation of the anatomic imaging data.

2. The method of claim 1, wherein modifying the first digital representation of the anatomic imaging data is based on a characteristic associated with the patient.

3. The method of claim 2, wherein the characteristic associated with the patient includes a stiffness of the portion of the patient's blood vessel.

4. The method of claim 1, wherein modifying the first digital representation of the anatomic imaging data is based on a characteristic associated with the patient-specific prosthesis.

5. The method of claim 4, wherein the characteristic associated with the patient-specific prosthesis includes a stiffness of a portion of the patient-specific prosthesis.

6. The method of claim 1, wherein modifying the first digital representation of the anatomic imaging data is based on a characteristic associated with a manner of introducing the patient-specific prosthesis to the portion of the patient.

7. The method of claim 1, wherein the portion of the patient's blood vessel is at least a portion of the patient's abdominal aorta and the patient-specific prosthesis is an endovascular stent graft configured to stent an aneurysm formed by a portion of the abdominal aorta.

8. The method of claim 1, wherein the first digital representation of the anatomic imaging data is associated with the portion of the patient's blood vessel in a first configuration, and
   the second digital representation of the anatomic imaging data is associated with the portion of the patient's blood vessel in a second configuration, the portion of the patient's blood vessel being transitioned from the first configuration to the second configuration in response to at least one of an insertion of the patient-specific prosthesis and an indwelling of the patient-specific prosthesis.

9. The method of claim 1, wherein modifying the first digital representation of the anatomic imaging data is based on a centerline of the portion of the patient's blood vessel in the second configuration.

10. The method of claim 1, wherein generating the patient-specific prosthesis includes defining at least one indicator, the at least one indicator being associated with an anatomic feature included in the portion of the patient's blood vessel.

11. The method of claim 1, wherein the portion of the patient's blood vessel is at least a portion of the patient's abdominal aorta and generating the patient-specific prosthesis includes defining at least one fenestration in the patient-specific prosthesis, the at least one fenestration being associated with a branch vasculature stemming from the patient's abdominal aorta.

12. The method of claim 11, wherein the patient-specific prosthesis is a patient-specific stent graft.

13. The method of claim 11, wherein the at least one fenestration is formed in the patient-specific prosthesis via at least one of a mechanical cutting process, a mechanical punching process, a laser cutting process, a water jet cutting process, and a drilling process.

14. The method of claim 11, wherein generating the patient-specific prosthesis includes coupling a radiopaque material to a portion of the patient-specific prosthesis associated with the at least one fenestration.

15. The method of claim 1, further comprising:
defining a plurality of digital representations of the anatomic imaging data based on modifying the first digital representation of the anatomic imaging data, the second digital representation being from the plurality of digital representations of the anatomic imaging data.

16. The method of claim 1, wherein modifying the first digital representation of the anatomic imaging data is based on a predetermined data set, the method further comprising:
updating the predetermined data set based on data associated with the second digital representation.

17. A method comprising:
receiving anatomic imaging data representative of a portion of a patient's blood vessel, the portion of the patient's blood vessel having a branch blood vessel extending from the portion of the patient's blood vessel;
defining a first digital representation of the portion of the patient's blood vessel based on the anatomic imaging data, the first digital representation including data representative of a first location of an anatomic feature of the patient's blood vessel;
modifying the first digital representation of the portion of the patient's blood vessel to generate a second digital representation of the portion of the patient's blood vessel, the second digital representation including data representative of a second location of the anatomic feature of the patient's blood vessel, the second location different than the first location; and
generating a patient-specific prosthetic based on the second digital representation of the portion of the patient's blood vessel, the patient-specific prosthetic having a wall defining a lumen, the wall of the patient-specific prosthetic defining an aperture corresponding to a location of the branch blood vessel in the second digital representation.

18. The method of claim 17, wherein modifying the first digital representation of the portion of the patient's blood vessel is based on a characteristic associated with the patient.

19. The method of claim 18, wherein the characteristic associated with the patient includes the stiffness of a portion of the portion of the patient's blood vessel.

20. The method of claim 17, wherein modifying the first digital representation of the portion of the patient's blood vessel is based on a characteristic associated with the patient-specific prosthetic.

21. The method of claim 20, wherein the characteristic associated with the patient-specific prosthetic includes the stiffness of a portion of the patient-specific prosthetic.

22. The method of claim 17, wherein modifying the first digital representation of the portion of the patient's blood vessel is based on a characteristic associated with a method of introducing the patient-specific prosthetic to the portion of the patient's blood vessel.

23. The method of claim 17, wherein the first digital representation of the portion of the patient's blood vessel is associated with the portion of the patient's blood vessel in a first configuration and the second digital representation of the portion of the patient's blood vessel is associated with the portion of the patient's blood vessel in a second configuration, the portion of the patient's blood vessel being transitioned from the first configuration to the second configuration in response to insertion of the patient-specific prosthetic.

24. The method of claim 17, wherein the modifying the first digital representation of the portion of the patient's blood vessel is based on a centerline of the portion of the patient's blood vessel in the second configuration.

25. A method comprising:
receiving anatomic imaging data representative of a portion of a patient's aorta, the portion of the patient's aorta having a first branch blood vessel extending from the aorta and a second branch blood vessel extending from the aorta;
defining a first digital representation of the portion of the patient's aorta, the first branch blood vessel, and the second branch blood vessel based on the anatomic imaging data, the first digital representation including data representative of a first location of an anatomic feature of the patient's aorta;
modifying the first digital representation of the portion of the patient's aorta to generate a second digital representation of the portion of the patient's aorta, the first branch blood vessel, and the second branch blood vessel, the second digital representation including data representative of a second location of the anatomic feature of the patient's aorta, the second location different than the first location; and
generating a patient-specific prosthetic based on the second digital representation of the portion of the patient's aorta.

26. The method of claim 25, wherein the first branch blood vessel is a renal artery.

27. The method of claim 26, wherein the second branch blood vessel is a renal artery.

28. The method of claim 25, wherein the second branch blood vessel is a superior mesenteric artery.

29. The method of claim 25, wherein patient-specific prosthetic defines a first opening corresponding to a location of the first branch blood vessel in the second digital representation, and a second opening corresponding to a location of the second branch blood vessel in the second digital representation.

* * * * *